(12) United States Patent
Sato

(10) Patent No.: US 10,729,407 B2
(45) Date of Patent: Aug. 4, 2020

(54) ULTRASONIC DIAGNOSTIC APPARATUS, IMAGE PROCESSING APPARATUS, AND IMAGE PROCESSING METHOD

(71) Applicant: TOSHIBA MEDICAL SYSTEMS CORPORATION, Otawara-Shi (JP)

(72) Inventor: Takeshi Sato, Nasushiobara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 665 days.

(21) Appl. No.: 14/803,726

(22) Filed: Jul. 20, 2015

(65) Prior Publication Data

US 2015/0320395 A1 Nov. 12, 2015

Related U.S. Application Data

(63) Continuation of application No. PCT/JP2014/051300, filed on Jan. 22, 2014.

(30) Foreign Application Priority Data

Jan. 22, 2013 (JP) ................................. 2013-009637
Jan. 22, 2014 (JP) ................................. 2014-009794

(51) Int. Cl.
*A61B 8/08* (2006.01)
*A61B 8/00* (2006.01)
(Continued)

(52) U.S. Cl.
CPC ................ *A61B 8/488* (2013.01); *A61B 8/06* (2013.01); *A61B 8/461* (2013.01); *A61B 8/5207* (2013.01);
(Continued)

(58) Field of Classification Search
None
See application file for complete search history.

(56) References Cited

U.S. PATENT DOCUMENTS 5,379,771 A 1/1995 Kawasaki et al.
2005/0033170 A1* 2/2005 Angelsen ............ G01S 7/52038
600/437
(Continued)

FOREIGN PATENT DOCUMENTS

JP 06-285067 A 10/1994
JP 10-5214 A 1/1998
(Continued)

OTHER PUBLICATIONS

Jamieson et al. "Exploring Nonlinear feature Space Dimension Reduction and Data Representation in Breast CADx with Laplacian Eigenmaps and t-SNE", Med. Phys. 37(1), Jan. 2010 pp. 339-351 (Year: 2010).*

(Continued)

*Primary Examiner* — Angela M Hoffa
*Assistant Examiner* — Farouk A Bruce
(74) *Attorney, Agent, or Firm* — Oblon, McClelland, Maier & Neustadt, L.L.P.

(57) ABSTRACT

An ultrasonic diagnostic apparatus according to one embodiment includes correlation matrix calculating circuitry, calculating circuitry, image generating circuitry, and controlling circuitry. The correlation matrix calculating circuitry calculates a correlation matrix of a scanned region consisting of a plurality of scan lines, from a data array of pieces of reflection wave data collected from the same position by transmitting and receiving ultrasonic waves in the scanned region across a plurality of frames. The calculating circuitry calculates a filter coefficient for suppressing a clutter generated by a tissue, by performing principal component analysis using the correlation matrix, and by performing a matrix operation of approximating a clutter component as a principal component and of suppressing the clutter component. The image generating circuitry generates ultrasound
(Continued)

image data from blood flow information estimated using the filter coefficient. The controlling circuitry causes a display to display the ultrasound image data.

14 Claims, 18 Drawing Sheets

(51) Int. Cl.
*A61B 8/06* (2006.01)
*G01S 15/89* (2006.01)
*G01S 7/52* (2006.01)

(52) U.S. Cl.
CPC ...... *G01S 7/52085* (2013.01); *G01S 15/8977* (2013.01); *G01S 15/8979* (2013.01); *G01S 15/8981* (2013.01); *G01S 7/52074* (2013.01)

(56) References Cited

U.S. PATENT DOCUMENTS

| | | | | |
|---|---|---|---|---|
| 2005/0276506 | A1* | 12/2005 | Kwon | H04N 5/21 382/269 |
| 2006/0079782 | A1* | 4/2006 | Beach | A61B 5/02007 600/450 |
| 2007/0049824 | A1* | 3/2007 | Konofagou | A61B 8/08 600/437 |
| 2007/0239015 | A1 | 10/2007 | Sato | |
| 2008/0137969 | A1* | 6/2008 | Rueckert | G06K 9/6234 382/224 |
| 2008/0275340 | A1* | 11/2008 | Beach | A61B 8/0808 600/438 |
| 2010/0280384 | A1* | 11/2010 | Song | A61B 8/488 600/453 |
| 2011/0306886 | A1* | 12/2011 | Daft | A61B 8/0825 600/459 |
| 2014/0039317 | A1 | 2/2014 | Sato | |

FOREIGN PATENT DOCUMENTS

| | | |
|---|---|---|
| JP | 2007-222390 A | 9/2007 |
| JP | 2008-149153 A | 7/2008 |
| JP | 2010-259799 A | 11/2010 |
| JP | 2012-217804 A | 11/2012 |

OTHER PUBLICATIONS

Lovstakken, L., "Real-Time Adaptive Clutter Rejection Filtering in Color Flow Imaging Using Power Method Iterations", IEEE Transactions on Ultrasonics, Ferroelectronics, and Frequency Control, vol. 53, No. 9, Sep. 2006, pp. 1597-1608 (Year: 2006).*
Yu, A.C.H., Eigen-Based Clutter Filter Design for Ultrasound Color Flow Imaging: A Review, IEEE Transactions on Ultrasonics, Ferroelectrics, and Frequency Control, vol. 57, No. 5, May 2010, pp. 1096-1111 (Year: 2010).*
U.S. Appl. No. 14/039,972, filed Sep. 27, 2013, Sato.
International Search Report dated Apr. 28, 2014 in PCT/JP2014/051300 filed Jan. 22, 2014 with English translation.
Written Opinion dated Apr. 28, 2014 in PCT/JP2014/051300 filed Jan. 22, 2014.
Steinar Bjaerum, et al., "Optimal Adaptive Clutter Filtering in Color Flow Imaging" IEEE Ultrasonics Symposium, 1997, pp. 1223-1226.
Steinar Bjaerum, et al., "Clutter Filters Adapted to Tissue Motion in Ultrasound Color Flow Imaging" IEEE Transactions on Ultrasonics, Ferroelectrics, and Frequency Control, vol. 49, No. 6, Jun. 2002, pp. 693-704.
Lasse Lovstakken, et al., "Real-Time Adaptive Clutter Rejection Filtering in Color Flow Imaging Using Power Method Iterations" IEEE Transactions on Ultrasonics, Ferroelectrics, and Frequency Control, vol. 53, No. 9, Sep. 2006, pp. 1597-1608.
Office Action dated Jan. 8, 2019 in corresponding Japanese Patent Application No. 2017-180569.

* cited by examiner

| $TH_1$ | 1000000 dB |
|---|---|
| $TH_2$ | 1000000 dB |
| $TH_3$ | 20 dB |
| $TH_4$ | 15 dB |
| $TH_5$ | 10 dB |
| $TH_6$ | 5 dB |
| $TH_7$ | -1 dB |
| $TH_8$ | -1 dB |

WITH INTERPOLATION

WITHOUT INTERPOLATION

→ RASTER DIRECTION (n-2) FRAME (n-1) FRAME

TEMPORAL
DIRECTION n FRAME

ULTRASONIC DIAGNOSTIC APPARATUS, IMAGE PROCESSING APPARATUS, AND IMAGE PROCESSING METHOD

CROSS-REFERENCE TO RELATED APPLICATIONS

This application is a continuation of PCT international application Ser. No. PCT/JP2014/051300 filed on Jan. 22, 2014 which designates the United States, the entire contents of which are incorporated herein by reference, and which claims the benefit of priority from Japanese Patent Application No. 2013-009637, filed on Jan. 22, 2013, and Japanese Patent Application No. 2014-009794, filed on Jan. 22, 2014; the entire contents of which are incorporated herein by reference.

FIELD

Embodiments described herein relate generally to an ultrasonic diagnostic apparatus, an image processing apparatus, and an image processing method.

BACKGROUND

Ultrasonic diagnostic apparatuses have conventionally been widely used for diagnosing or observing blood flows in living organisms. An ultrasonic diagnostic apparatus generates and displays blood flow information using Doppler imaging, which visualizing ultrasonic reflection waves based on the Doppler shift. Examples of blood flow information generated and displayed by an ultrasonic diagnostic apparatus include color Doppler images and Doppler waveforms (Doppler spectrums).

A color Doppler image is an ultrasonic image achieved by color flow mapping (CFM). In CFM, an ultrasonic wave is transmitted and received a plurality of number of times along each of a plurality of scan lines. In CFM, an array of data acquired from the same position is then applied with moving target indicator (MTI) filtering so as to suppress the signals resulting from stationary or slow moving tissue structures (clutter signals) and to extract signals representing blood flows. In CFM, blood flow information such as velocity, variance, and power of blood flows are estimated based on the blood flow signals, and the resultant distribution of the estimation results is displayed as, for example, a two-dimensional color ultrasonic image (color Doppler image).

While a filter with a fixed coefficient, such as Butterworth infinite impulse response (IIR) filter or a polynomial regression filter, is usually used as an MTI filter, an adaptive MTI filter in which the coefficient is changed based on the input signal is also known.

An exemplary adaptive MTI filter calculates a tissue velocity from the signals before input to the MTI filter, and acquires signals having their phase difference cancelled out. The filter then selects one of MTI filter coefficients prepared in advance, based on the resultant signals. Another type of adaptive MTI filter generally referred to as an "eigenvector regression filter" is also known. To acquire a signal with its clutter component suppressed, this type of adaptive MTI filter calculates eigenvectors from a correlation matrix, and calculates the coefficient to be used in the MTI filter directly from the calculated eigenvectors. The approach is an application of the technique used in the principal component analysis, Karhunen-Loeve transform, or the eigenspace method. Also known as real-time implementation of the method that uses the "eigenvector regression filter" is a method using the "iterative power method" in calculating the eigenvectors.

The adaptive MTI filter described above calculates eigenvectors from a correlation matrix. The image quality of a video visualized with the adaptive MTI filter using eigenvectors, however, changes depending on what conditions the correlation matrix is calculated with. Therefore, the adaptive MTI filter using eigenvectors has not always resulted in a video with better image quality.

DETAILED DESCRIPTION

An ultrasonic diagnostic apparatus according to one embodiment includes correlation matrix calculating circuitry, calculating circuitry, image generating circuitry, and controlling circuitry. The correlation matrix calculating circuitry is configured to calculate a correlation matrix of a scanned region consisting of a plurality of scan lines, from a data array of pieces of reflection wave data collected from the same position by transmitting and receiving ultrasonic waves in the scanned region across a plurality of frames. The calculating circuitry is configured to calculate a filter coefficient for suppressing a clutter generated by a tissue, by performing principal component analysis using the correlation matrix, and by performing a matrix operation of approximating a clutter component as a principal component and of suppressing the clutter component. The image generating circuitry is configured to generate ultrasound image data from blood flow information estimated using the filter coefficient. The controlling circuitry is configured to cause a display to display the ultrasound image data.

Some embodiments of an ultrasonic diagnostic apparatus will now be explained in detail with reference to the accompanying drawings.

First Embodiment

Figure 1:
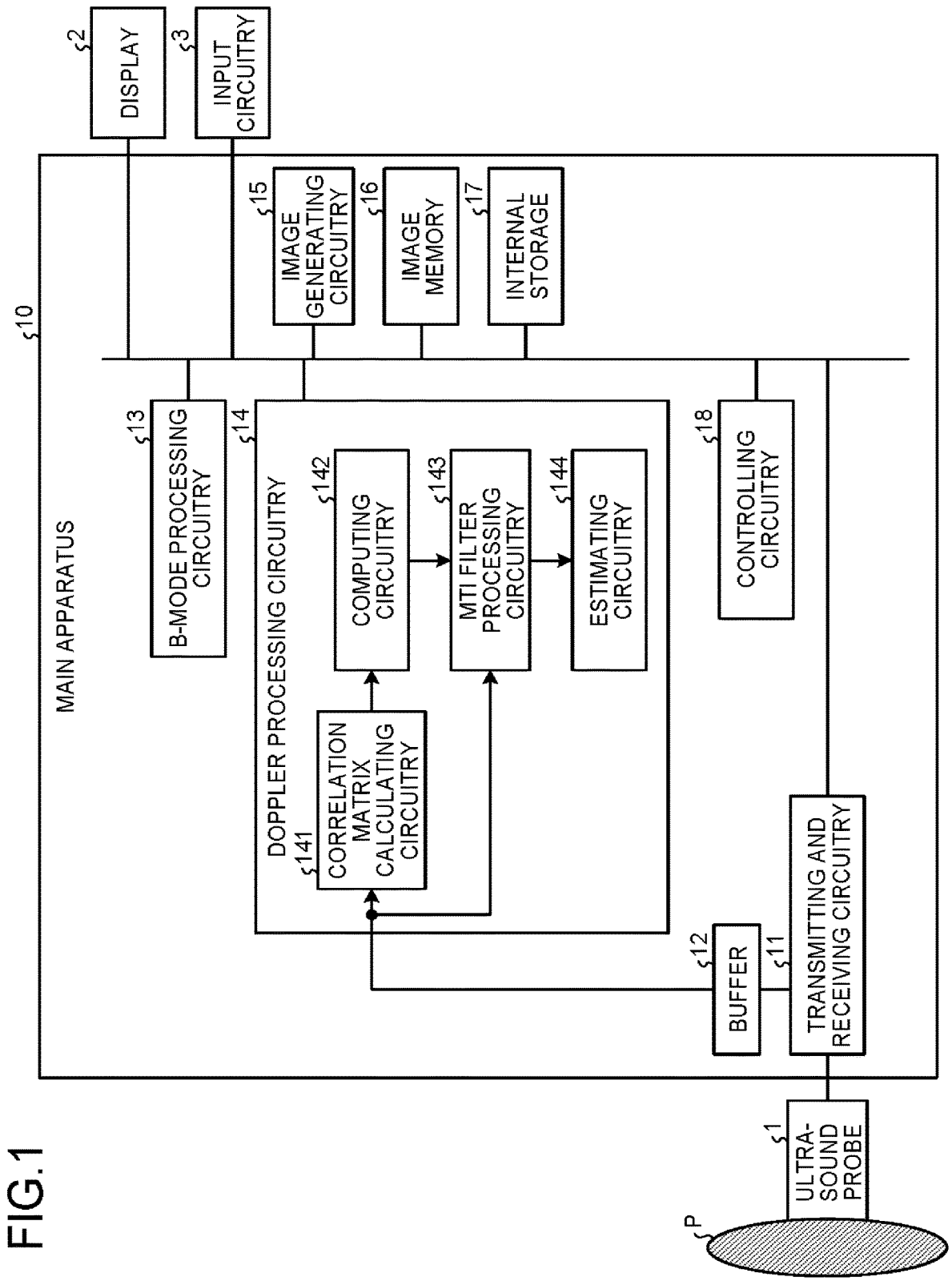
FIG. 1 is a block diagram illustrating an exemplary configuration of an ultrasonic diagnostic apparatus according to a first embodiment.

A configuration of an ultrasonic diagnostic apparatus according to a first embodiment will now be explained. FIG. 1 is a block diagram illustrating the exemplary configuration of the ultrasonic diagnostic apparatus according to the first embodiment. As illustrated in FIG. 1, the ultrasonic diagnostic apparatus according to the first embodiment includes an ultrasound probe 1, a display 2, input circuitry 3, and a main apparatus 10.

To transmit and to receive ultrasonic waves, the ultrasound probe 1 is connected to the main apparatus 10. The ultrasound probe 1 includes, for example, a plurality of piezoelectric transducer elements, and each of these piezoelectric transducer elements generates an ultrasonic wave based on a driving signal supplied by transmitting and receiving circuitry 11 included in the can apparatus 10. The piezoelectric transducer element in the ultrasound probe 1 also receives a reflection wave from a subject P and converts the reflection wave into an electric signal. The ultrasound probe 1 also includes a matching layer formed on the piezoelectric transducer elements, and a backing material for preventing the ultrasonic waves from propagating backwardly from the piezoelectric transducer elements. The ultrasound probe 1 is connected removably to the main apparatus 10.

Once the ultrasound probe 1 transmits an ultrasonic wave to the subject P, the ultrasonic wave reflects one after another on an acoustic impedance discontinuous plane of body tissues in the subject P, and the piezoelectric transducer element included in the ultrasound probe 1 receives the reflected wave as a reflection wave signal. The amplitude of the received reflection wave signal is dependent on the acoustic impedance of the discontinuous plane where the ultrasonic wave is reflected. When a transmitted ultrasonic pulse reflects on a moving surface such as a blood flow or a cardiac wall, the resultant reflection wave becomes subject to a frequency shift due to the Doppler shift. Such a frequency shift is dependent on the velocity component of the moving body with respect to the direction in which the ultrasonic wave is transmitted.

The first embodiment can be used in configurations in which the ultrasound probe 1 is a one-dimensional array probe that scans the subject P two dimensionally, and in which the ultrasound probe 1 is a mechanical four-dimensional probe or a two-dimensional array probe that scans the subject P three dimensionally.

The input circuitry 3 includes a mouse, a keyboard, a button, a panel switch, a touch command screen, a foot switch, a trackball, and a joystick. The input circuitry 3 receives various setting requests from an operator of the ultrasonic diagnostic apparatus, and transfers the received various setting requests to the main apparatus 10.

The display 2 displays a graphical user interface (GUI) for allowing an operator of the ultrasonic diagnostic apparatus to enter various setting requests using the input circuitry 3, and ultrasound image data and the like generated in the main apparatus 10, for example.

The main apparatus 10 is an apparatus that generates ultrasound image data based on the reflection wave signals received by the ultrasound probe 1. The main apparatus 10 illustrated in FIG. 1 is an apparatus capable of generating two-dimensional ultrasound image data based on two-dimensional reflection wave signals, and three-dimensional ultrasound image data based on three-dimensional reflection wave signals. The first embodiment can also be used in a configuration in which the main apparatus 10 is specialized for two-dimensional data.

As illustrated in FIG. 1, the main apparatus 10 includes the transmitting and receiving circuitry 11, a buffer 12, B-mode processing circuitry 13, Doppler processing circuitry 14, image generating circuitry 15, an image memory 16, an internal storage 17, and controlling circuitry 18.

The transmitting and receiving circuitry 11 controls transmissions and receptions of ultrasonic waves from and by the ultrasound probe 1 based on instructions from the controlling circuitry 18, which is described later. The transmitting and receiving circuitry 11 includes a pulse generator, a transmission delay circuit, and a puller, and supplies driving signals to the ultrasound probe 1. The pulse generator generates a rate pulse for generating an ultrasonic wave to be transmitted repeatedly at a predetermined pulse repetition frequency (PRF). The transmission delay circuit delays the rate pulse generated by the pulse generator, by a delay time required for each of the piezoelectric transducer elements to converge the ultrasonic wave generated by the ultrasound probe 1 into a beam and to determine transmission directivity. The puller applies a driving signal (driving pulse) to the ultrasound probe 1 at the timing of the rate pulse. In other words, by changing the delay time added to a rate pulse, the transmission delay circuit desirably adjusts the direction in which the piezoelectric transducer element surface outputs the ultrasonic wave.

The transmitting and receiving circuitry 11 has a function capable of instantaneously changing the transmission frequency, the transmission driving voltage, and the like to allow a predetermined scan sequence to be executed based on instructions from the controlling circuitry 18, which is described later. The transmission driving voltage is changed by a linear amplifying oscillating circuit capable of switching its value instantaneously, or a mechanism that electrically switches a plurality of power source units.

The transmitting and receiving circuitry 11 also includes an amplifier circuit, an analog-to-digital (A/D) converter, a receiving delay circuit, an adder, and a quadrature detector circuit, and generates reflection wave data by performing various processes to the reflection wave signal received by the ultrasound probe 1. The amplifier circuit amplifies the reflection wave signal on each channel, and performs a gain correction to the signal. The A/D converter A/D-converts the reflection wave signal applied with the gain correction. The receiving delay circuit adds a receiving delay time required for determining reception directivity to the digital data. The adder adds the reflection wave signals with the receiving delay time added by the receiving delay circuit. In the reflection wave signals, a component reflecting in the direction matching the reception directivity is emphasized by this addition performed by the adder.

The quadrature detector circuit converts the output signal from the adder into an in-phase (I) signal and a quadrature-phase (Q) signal in the baseband bandwidth. The quadrature detector circuit then stores the I signal and the Q signal (hereinafter, referred to as I/Q signals) in the buffer 12 as the reflection wave data. The quadrature detector circuit may also convert the output signal from the adder into a radio frequency (RF) signal and then store the RF signal in the buffer 12. The I/Q signals or the RF signal is a signal including phase information (received signal). Hereinafter, the reflection wave data output from the transmitting and receiving circuitry 11 is sometimes referred to as a received signal.

When the subject P is scanned two dimensionally, the transmitting and receiving circuitry 11 causes the ultrasound probe 1 to transmit a two-dimensional ultrasound beam. The transmitting and receiving circuitry 11 then generates two-dimensional reflection wave data from the two-dimensional reflection wave signals received by the ultrasound probe 1. When the subject P is scanned three dimensionally, the transmitting and receiving circuitry 11 causes the ultrasound probe 1 to transmit a three-dimensional ultrasound beam. The transmitting and receiving circuitry 11 then generates three-dimensional reflection wave data from the three-dimensional reflection wave signals received by the ultrasound probe 1.

The buffer 12 is a buffer for temporarily storing therein reflection wave data (I/Q signals) generated by the transmitting and receiving circuitry 11. Specifically, the buffer 12 stores therein I/Q signals corresponding to several frames or several volumes. The buffer 12 is, for example, a first-in/first-out (FIFO) memory, and stores therein I/Q signals corresponding to a predetermined number of frames. When the transmitting and receiving circuitry 11 then generates I/Q signals for a new frame, for example, the buffer 12 discards the I/Q signals corresponding to the oldest frame, and stores the I/Q signals corresponding to the newly generated frame.

The B-mode processing circuitry 13 and the Doppler processing circuitry 14 are signal processing circuitry that perform various types of signal processing to the reflection wave data generated from the reflection wave signals by the transmitting and receiving circuitry 11. The B-mode processing circuitry 13 performs logarithmic amplification, envelope detection, logarithmic compression, and the like to the reflection wave data (I/Q signals) read from the buffer 12, and generates data representing signal intensities corresponding to a plurality of respective sampling points as luminance (B-mode data).

The B-mode processing circuitry 13 is capable of changing the frequency bandwidth to be visualized by filtering the detected frequencies. The ultrasonic diagnostic apparatus according to the first embodiment can perform harmonic imaging such as contrast harmonic imaging (CHI) or tissue harmonic imaging (THI) using this function of the B-mode processing circuitry 13. In other words, the B-mode processing circuitry 13 separates the reflection wave data acquired from the subject P having received an injection of contrast agent into that corresponding to a harmonic component having a reflection source in the contrast agent (extremely small bubbles) (harmonic data or subharmonic data) and that corresponding to a fundamental component having a reflection source in the tissues of the subject P (fundamental wave data). The B-mode processing circuitry 13 can therefore use the reflection wave data (received signals) representing the harmonic component to generate the B-mode data from which contrast image data is to be generated.

The ultrasonic diagnostic apparatus according to the first embodiment can perform THI using the filtering function of the B-mode processing circuitry 13. In other words, the B-mode processing circuitry 13 is capable of separating harmonic data or subharmonic data that is reflection wave data (received signals) corresponding to the harmonic component from the reflection wave data of the subject P. The B-mode processing circuitry 13 can therefore generate B-mode data, from which tissues image data having noise components removed is to be generated, using the reflection wave data (received signal) of the harmonic components.

For harmonic imaging such as CHI or THI, the B-mode processing circuitry 13 may use an approach other than the filtering mentioned above to extract harmonic components. In harmonic imaging, imaging such as amplitude modulation (AM) imaging, phase modulation (PM) imaging, or what is called AMPM imaging using a combination of the AM and the PM is used. In the AM imaging, the PM imaging, and the AMPM imaging, an ultrasonic wave with a different amplitude or phase is transmitted a plurality of number of times along the same scan line. This allows the transmitting and receiving circuitry 11 to generate and to output a plurality of pieces of reflection wave data (received signals) for one scan line. The B-mode processing circuitry 13 then extracts harmonic components by adding or subtracting the pieces of reflection wave data (received signals), corresponding to each of the scan lines, in a manner suitable for the modulation in use. The ID-mode processing circuitry 13 then generates B-mode data by performing processing such as envelope detection to the reflection wave data (received signal) of the harmonic components.

For example, when used is PM, the transmitting and receiving circuitry 11 causes the ultrasound probe 1 to transmit a ultrasonic wave with an opposite polarity and the same amplitude twice, e.g., (−1,1), along each of the scan lines, following a scan sequence specified by the controlling circuitry 18. The transmitting and receiving circuitry 11 then generates a received signal for the transmission of "−1", and another received signal for the transmission of "1". The B-mode processing circuitry 13 then combines these two received signals. In this manner, the B-mode processing circuitry 13 generates a signal mainly representing a second-order harmonic component, with a fundamental component removed. The B-mode processing circuitry 13 then generates B-mode data for THI or CHI by performing processing such as envelope detection to the signal.

As another example, THI, which performs imaging of a video using a second-order harmonic component and a differential component included in received signals, has been put into practice. In the type of imaging using a differential component, for example, the ultrasound probe 1 transmits an ultrasonic wave with a waveform resulting from synthesizing a first fundamental wave with a center frequency of "f1" and a second fundamental wave with a center frequency "f2" that is higher than "f1". This synthetic waveform is a synthesis of the waveform of the first fundamental wave and the waveform of the second fundamental wave, with their phases adjusted in such a manner that the resultant differential component has the same polarity as the second-order harmonic component. The transmitting and receiving circuitry 11 transmits a transmission ultrasonic wave having such a synthetic waveform twice, with their phase reversed. In this example, the B-mode processing circuitry 13 extracts the harmonic component mainly representing the differential component and the second-order harmonic component with the fundamental component removed by adding the two received signals, and then performs processing such as envelope detection.

The Doppler processing circuitry 14 generates data that is extraction of movement information of moving bodies within a scanned region, such movement information being based on Doppler shift (Doppler data), by analyzing the frequencies of the reflection wave data read from the buffer 12. Specifically, the Doppler processing circuitry 14 generates Doppler data such as average velocity, average variance, and average power, as movement information of moving bodies, at each of a plurality of sampling points. Examples of a moving body herein include blood flows, tissues such as those of a cardiac wall, and contrast agent. As the movement information of a blood flow (blood flow information), the Doppler processing circuitry 14 according to the embodiment generates Doppler data that is estimations of average velocity, average variance, average power, and the like of the blood flow at each of a plurality of sampling points.

The ultrasonic diagnostic apparatus according to the embodiment can perform color Doppler imaging, which is also referred to as color flow mapping (CFM), using the function of the Doppler processing circuitry 14. In CFM, an ultrasonic wave is transmitted and received a plurality of number of times along each of a plurality of scan line. In CFM, a moving target indicator (MTI) filter is applied to a data array acquired from the same position to suppress signals resulting from stationary or slow moving tissue structures (clutter signals), and to extract signals representing a blood flow. In CFM, blood flow information such as velocity, variance, power, and the like of the blood flow is then estimated from the blood flow signals. The image generating circuitry 15, which is described later, then generates ultrasound image data (color Doppler image data) that is a two-dimensional color representation of the distribution of the estimation results, for example, and the display 2 displays the color Doppler image data.

While a filter with a fixed coefficient such as Butterworth infinite impulse response (IIR) filter or a polynomial regression filter is usually used as the MTI filter, the Doppler processing circuitry 14 according to the embodiment uses an adaptive MTI filter, which changes the coefficient depending on the input signal. Specifically, the Doppler processing circuitry 14 according to the embodiment uses a filter generally referred to as an "eigenvector regression filter" as the adaptive MTI filter. Hereinafter, an "eigenvector regression filter" that is an adaptive MTI filter using eigenvectors is referred to as an "eigenvector MTI filter".

For the eigenvector MTI filter, eigenvectors are calculated from a correlation matrix, and a coefficient to be used in suppressing the clutter components is calculated from the calculated eigenvectors. This approach is an application of the technique used in the principal component analysis, the Karhunen-Loeve transform, or the eigenspace method.

The Doppler processing circuitry 14 according to the first embodiment that uses an eigenvector MTI filter includes correlation matrix calculating circuitry 141, computing circuitry 142, MTI filter processing circuitry 143, and estimating circuitry 144, as illustrated in FIG. 1. The correlation matrix calculating circuitry 141 calculates a correlation matrix of a scanned region, from an array of consecutive reflection wave data acquired from the same position (the same sampling point). The computing circuitry 142 calculates the eigenvalues of the correlation matrix, and eigenvectors corresponding to the respective eigenvalues, for example. The computing circuitry 142 then calculates a matrix by reducing the rank of a matrix consisting of the eigenvectors arranged accordingly to the size of the respective eigenvalues, as a filter matrix for suppressing clutter components.

From a data array consisting of consecutive reflection wave data acquired from the same position (the same sampling point), the MTI filter processing circuitry 143 extracts and outputs a data array representing blood flow signals resulting from the blood flows having its clutter components suppressed using a filter matrix. Using the data output from the MTI filter processing circuitry 143, the estimating circuitry 144 estimates the blood flow information by performing an operation such as an autocorrelation operation, and outputs the estimated blood flow information as Doppler data. Specific processes performed by the Doppler processing circuitry 14 according to the first embodiment will be explained later in detail.

The B-mode processing circuitry 13 and the Doppler processing circuitry 14 illustrated in FIG. 1 are capable of processing both of two-dimensional reflection wave data and three-dimensional reflection wave data. In other words, the B-mode processing circuitry 13 generates two-dimensional B-mode data from two-dimensional reflection wave data, and generates three-dimensional B-mode data from three-dimensional reflection wave data. The Doppler processing circuitry 14 also generates two-dimensional Doppler data from two-dimensional reflection wave data, and generates three-dimensional Doppler data from three-dimensional reflection wave data.

The image generating circuitry 15 generates ultrasound image data from the data generated by the B-mode processing circuitry 13 and the Doppler processing circuitry 14. Based on the two-dimensional B-mode data generated by the B-mode processing circuitry 13, the image generating circuitry 15 generates two-dimensional B-mode image data representing the intensities of the reflection waves as luminance. Based on the two-dimensional Doppler data generated by the Doppler processing circuitry 14, the image generating circuitry 15 generates two-dimensional Doppler image data visualizing the blood flow information. The two-dimensional Doppler image data is image data representing velocity, variance, power, or a combination thereof. The Doppler image data generated by the image generating circuitry 15 is either a piece of color Doppler image data representing a piece of blood flow information in colors, or Doppler image data representing a piece of blood flow information in a gray scale.

The image generating circuitry 15 generates ultrasound image data to be displayed, generally by converting (scan-converting) an array of ultrasound scan line signals into an array of scan-line signals in a video format, an example of which is a format for a television. Specifically, the image generating circuitry 15 generates ultrasound image data to be displayed by performing a coordinate conversion suitable for the ultrasound scan mode used by the ultrasound probe 1. In addition to the scan conversion, the image generating circuitry 15 also performs, as various types of image processing, image processing for re-generating average luminance image using a plurality of image frames applied with scan conversion (smoothing process), and image processing applying a differential filter to the image (edge emphasizing process), for example. The image generating circuitry 15 also synthesizes character information representing various parameters, scales, body marks, and the like to the ultrasound image data.

In other words, the B-mode data and the Doppler data are ultrasound image data not applied with scan conversion, and the data generated by the image generating circuitry 15 is ultrasound image data applied with scan conversion and to be displayed. The B-mode data and the Doppler data are also referred to as raw data. The image generating circuitry 15 generates two-dimensional ultrasound image data to be displayed from the two-dimensional ultrasound image data not applied with scan conversion.

The image generating circuitry 15 also generates three-dimensional B-mode image data by performing coordinate conversion to the three-dimensional B-mode data generated by the B-mode processing circuitry 13. The image generating circuitry 15 also generates three-dimensional Doppler image data by performing coordinate conversion to three-dimensional Doppler data generated by the Doppler processing circuitry 14. The image generating circuitry 15 generates "three-dimensional B-mode image data or three-dimensional Doppler image data" as "three-dimensional ultrasound image data (volume data)".

To generate various types of two-dimensional image data for displaying volume data on the display 2, the image generating circuitry 15 also performs a rendering process to the volume data. An example of the rendering process performed by the image generating circuitry 15 includes a process of generating a multi-planer reconstruction (MPR) image data by performing multi-planer reconstruction (MPR) to the volume data. Another example of the rendering process performed by the image generating circuitry 15 includes volume rendering (VR) in which two-dimensional image data reflected with three-dimensional information is generated.

The image memory 16 is a memory storing therein image data to be displayed generated by the image generating circuitry 15. The image memory 16 may also store therein data generated by the B-mode processing circuitry 13 and the Doppler processing circuitry 14. An operator can read the B-mode data and the Doppler data stored in the image memory 16 after making a diagnosis, for example. The image generating circuitry 15 turns these pieces of data into ultrasound image data to be displayed. The image memory 16 may also store therein the reflection wave data outputs from the transmitting and receiving circuitry 11.

The internal storage 17 stores therein a control program for transmitting and receiving ultrasonic waves, a control program for image processing, and a control program for processing the data for displaying, diagnostic information (such as patient ID and observations by physicians), and various types of data such as a diagnostic protocol or various body marks, for example. The internal storage 17 is also used to store the image data stored in the image memory 16, as required. The data stored in the internal storage 17 may be transferred to an external device via an interface not illustrated. The internal storage 17 may also store therein data received from an external device via an interface not illustrated.

The controlling circuitry 18 controls the entire processing performed by the ultrasonic diagnostic apparatus. Specifically, the controlling circuitry 18 controls the processes performed by the transmitting and receiving circuitry 11, the B-mode processing circuitry 13, the Doppler processing circuitry 14, and the image generating circuitry 15, based on various setting requests entered by an operator via the input circuitry 3, various control programs read from the internal storage 17, and various types of data. For example, the controlling circuitry 18 controls the ultrasound scan by controlling the ultrasound probe 1 via the transmitting and receiving circuitry 11. In CFM, usually, B-mode image data that is tissues image data is displayed together with color Doppler image data that is blood flow image data. To display these pieces of image data, the controlling circuitry 18 causes the ultrasound probe 1 to perform first ultrasound scan on a first scanned region to acquire the blood flow information. The first ultrasound scan is ultrasound scan for collecting the color Doppler image data in the Doppler mode, for example. The controlling circuitry 18 also causes the ultrasound probe 1 to perform second ultrasound scan, in addition to the first ultrasound scan, to acquire the shape of tissues in a second scanned region. The second ultrasound scan is ultrasound scan for collecting B-mode image data in the B-mode, for example.

The controlling circuitry 18 causes the ultrasound probe 1 to perform the first ultrasound scan and the second ultrasound scan by causing the transmitting and receiving circuitry 11 to control the ultrasound probe 1. The first scanned region and the second scanned region may be the same region. The first scanned region may also be smaller than the second scanned region, or the second scanned region may be smaller than the first scanned region.

The controlling circuitry 18 also controls to display the ultrasound image data to be displayed stored in the image memory 16 or the internal storage 17 onto the display 2. The units such as the transmitting and receiving circuitry 11 in the main apparatus 10 may be implemented as hardware such as an integrated circuit, or may be implemented as a computer program in which such circuitry are implemented as software modules.

Figure 2:
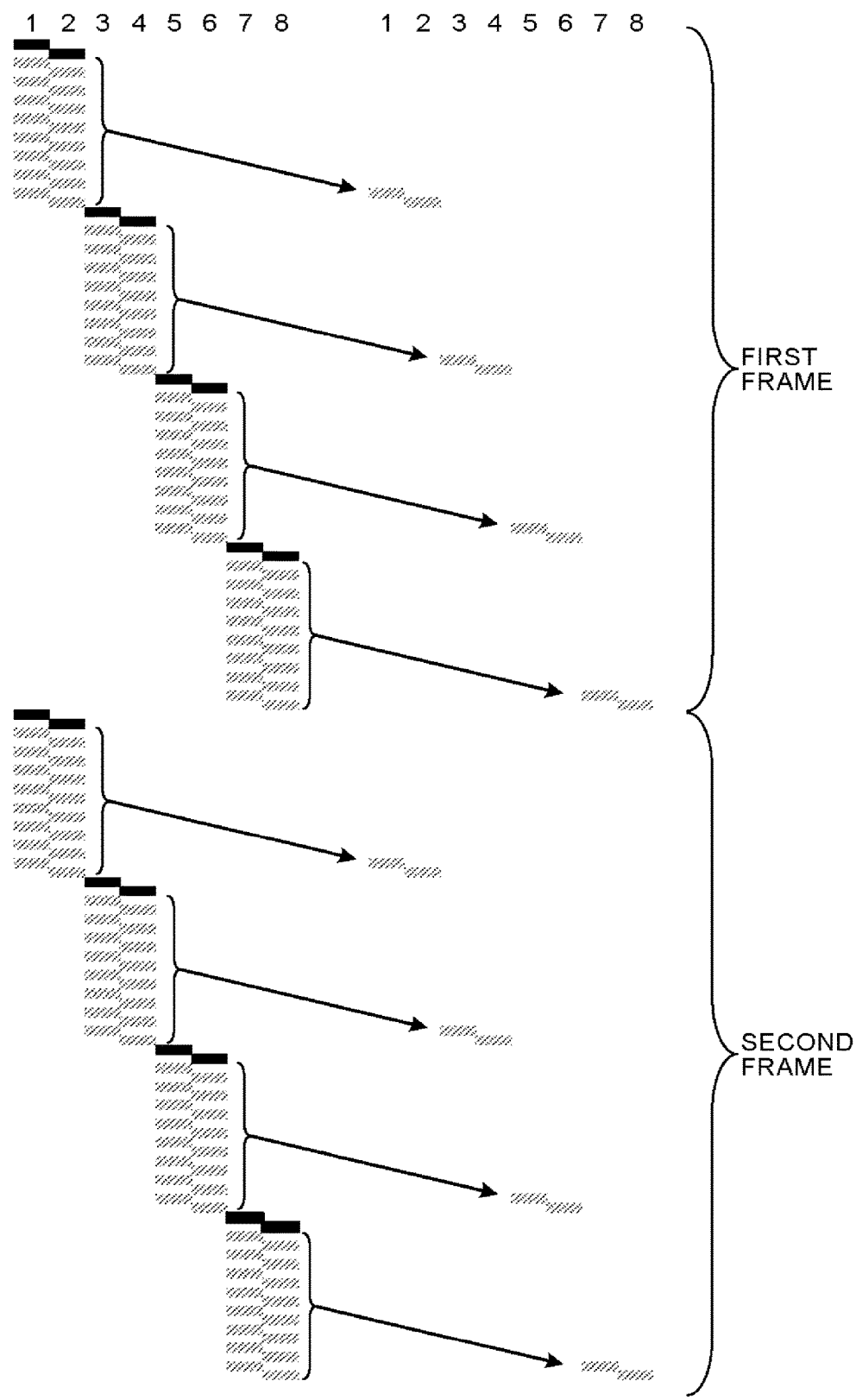
FIG. 2 and FIG. 3 are schematics for explaining the conventional technology.
Figure 3:
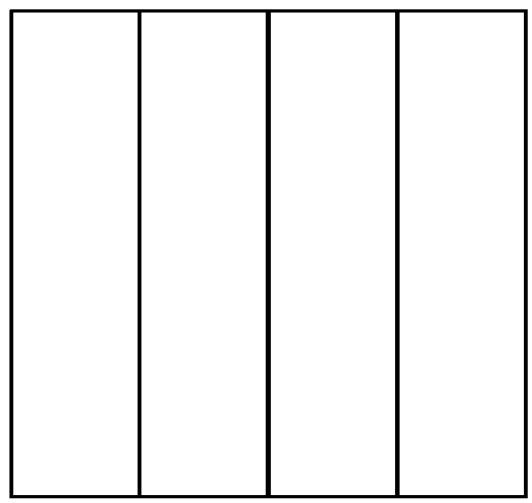

The overall configuration of the ultrasonic diagnostic apparatus according to the first embodiment is explained above. With such a configuration, the ultrasonic diagnostic apparatus according to the first embodiment performs CFM using blood flow information (Doppler data) estimated using an eigenvector MTI filter. As mentioned earlier, the Doppler processing circuitry 14 using the eigenvector MTI filter calculates eigenvectors from a correlation matrix. The image quality of Doppler image data visualized with the eigenvector MTI filter changes depending on what conditions the correlation matrix is calculated with. Therefore, there have been some cases in which no improvement is achieved in the image quality of an image visualized with the adaptive MTI filter using eigenvectors. One example will now be explained with reference to FIGS. 2 and 3. FIGS. 2 and 3 are schematics for explaining the conventional technology.

In the ordinary color Doppler imaging, a transmission and reception of an ultrasonic wave is repeated a plurality of number of times in the same direction, and a blood flow signal is extracted from each of the received signals. A data array acquired from the reflection wave signals (reflection wave data) acquired by transmitting and receiving the ultrasonic waves to and from the same position is referred to as a packet. A packet size represents the number of an ultrasonic wave transmitted and received along the same direction to acquire blood flow information for one frame. The packet size generally used in the color Doppler imaging is from five to 16 or so. With a larger packet size, the performance of the eigenvector MTI filter is improved, but the frame size is reduced.

In the conventional color Doppler imaging, to allow a blood flow at a low flow rate to be detected at a higher resolution by reducing a aliasing velocity, what is called alternating ultrasound scan has been practiced. With the alternating scan, however, the first scanned region for collecting Doppler data is divided into a plurality of scan blocks, and a time lag is introduced between the scan blocks. Therefore, when the eigenvector MTI filter is used, the Doppler processing circuitry 14 needs to calculate a correlation matrix of each of the scan blocks so that different MTI filtering can be applied to the respective blocks. Therefore, the conventional color Doppler imaging has resulted in ultrasound image data with abrupt change across the border between the scan blocks.

FIG. 2 illustrates an exemplary alternating scan. Illustrated in FIG. 2 is an example in which the first scanned region is the same as the second scanned region, and the scanned region consists of eight scan lines from a first scan line to an eighth scan line. In FIG. 2, the eight scan lines are indicated as "1, 2, 3, 4, 5, 6, 7, and 8", respectively, in the azimuth direction (in the direction in which the piezoelectric transducer elements are arranged in the ultrasound probe 1). In FIG. 2, the second ultrasound scan for the B-mode imaging is represented by a black rectangle, and the first ultrasound scan for Doppler mode imaging is represented by a hatched rectangle.

In the alternating scan illustrated in FIG. 2, the second ultrasound scan is performed along the first scan line, and then performed along the second scan line. The first ultrasound scan is then performed along the first scan line, and then along the second scan line, and this first ultrasound scan is repeated eight times. Output from this scan sequence are pieces of blood flow information corresponding to the first scan line and the second scan line. In the alternating scan illustrated in FIG. 2, the second ultrasound scan is performed along the third scan line, and then performed along the fourth scan line. The first ultrasound scan is then performed along the third scan line, and then along the fourth scan line, and this first ultrasound scan is repeated eight times. Output from this scan sequence are pieces of blood flow information corresponding to the third scan line and the fourth scan line.

In the alternating scan illustrated in FIG. 2, the second ultrasound scan is performed along the fifth scan line, and then performed along the sixth scan line. The first ultrasound scan is then performed along the fifth scan line, and then along the sixth scan line, and this first ultrasound scan is repeated eight times. Output from this scan sequence are pieces of blood flow information corresponding to the fifth scan line and the sixth scan line. In the alternating scan illustrated in FIG. 2, the second ultrasound scan is performed along the seventh scan line, and then performed along the eighth scan line. The first ultrasound scan is then performed along the seventh scan line, and then along the eighth scan line, and this first ultrasound scan is repeated eight times. Output from this scan sequence are pieces of blood flow information corresponding to the seventh scan line and the eighth scan line.

As a result of the process described above, B-mode image data and color Doppler image data for a first frame are generated and displayed. Image data corresponding to a second frame and thereafter is generated and displayed by repeating this process illustrated in FIG. 2. This alternating scan, illustrated in FIG. 2, is two-step alternating scan in which two adjacent scan lines are scanned alternatingly, and uses a packet size of "8". In the alternating scan illustrated in FIG. 2, because a piece of data is output for one packet, one frame is displayed upon completion of the scan corresponding to one frame. In other words, in this alternating scan, the number of frames displayed is always the same as the number of scan frames.

In the alternating scan illustrated in FIG. 2, because two out of the eight scan lines making up a scanned region for Doppler mode imaging are scanned alternatingly, the scanned region for Doppler mode imaging is divided into four scan blocks, as illustrated in FIG. 3. Because the Doppler data representing each of these scan blocks is generated upon completion of 8×2=16 sets of ultrasonic wave transmission and reception, these scan blocks appears as discontinuous in the Doppler image data resultant of the alternating scan illustrated in FIG. 2.

To improve the image quality of an image visualized from the blood flow information using an eigenvector MTI filter, in the first embodiment, the ultrasound scan used for Doppler mode imaging, which does not need to divide the scanned region into scan blocks, is used.

Specifically, the first ultrasound scan performed in the first embodiment is achieved by transmitting and receiving an ultrasonic wave repeatedly in a scanned region consisting of a plurality of scan lines in such a manner that the reflection wave data from the same position can be collected for a plurality of frames. More specifically, the first ultrasound scan according to the first embodiment is achieved by repeating a transmission and reception of an ultrasonic wave along each of a plurality of scan lines making up the scanned region. Such a scan mode is the same as that of the second ultrasound scan performed in the ordinary B-mode imaging, and is the same as that used in the CFM to improve the frame rate. Hereinafter, the first ultrasound scan described above is referred to as "high-frame-rate ultrasound scan" and the CFM performed with the "high-frame-rate ultrasound scan" is referred to as "high-frame-rate imaging".

In the high-frame-rate imaging, an array of data representing the same position can be processed across a plurality of frames in the frame direction (temporal direction). The high-frame-rate imaging, for example, allows the MTI filter to process data with an infinite length, rather than data with a finite length that is a packet. As a result, the high-frame-rate imaging can improve the performance of the MTI filter, and the blood flow information can be displayed at a higher rate.

Figure 4:
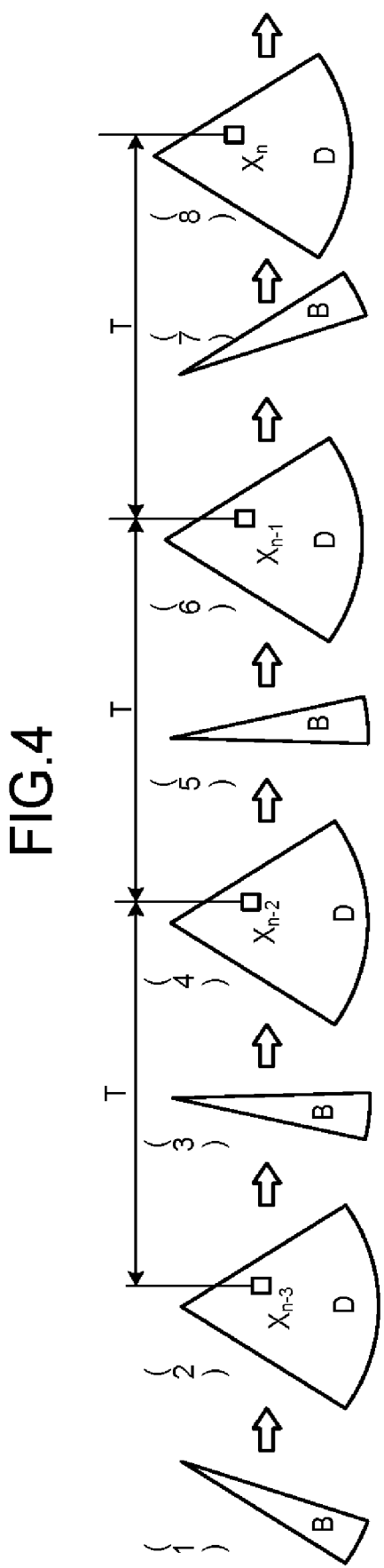
FIG. 4, FIG. 5 and FIG. 6 are schematics illustrating the exemplary ultrasound scan according to the first embodiment.
Figure 5:
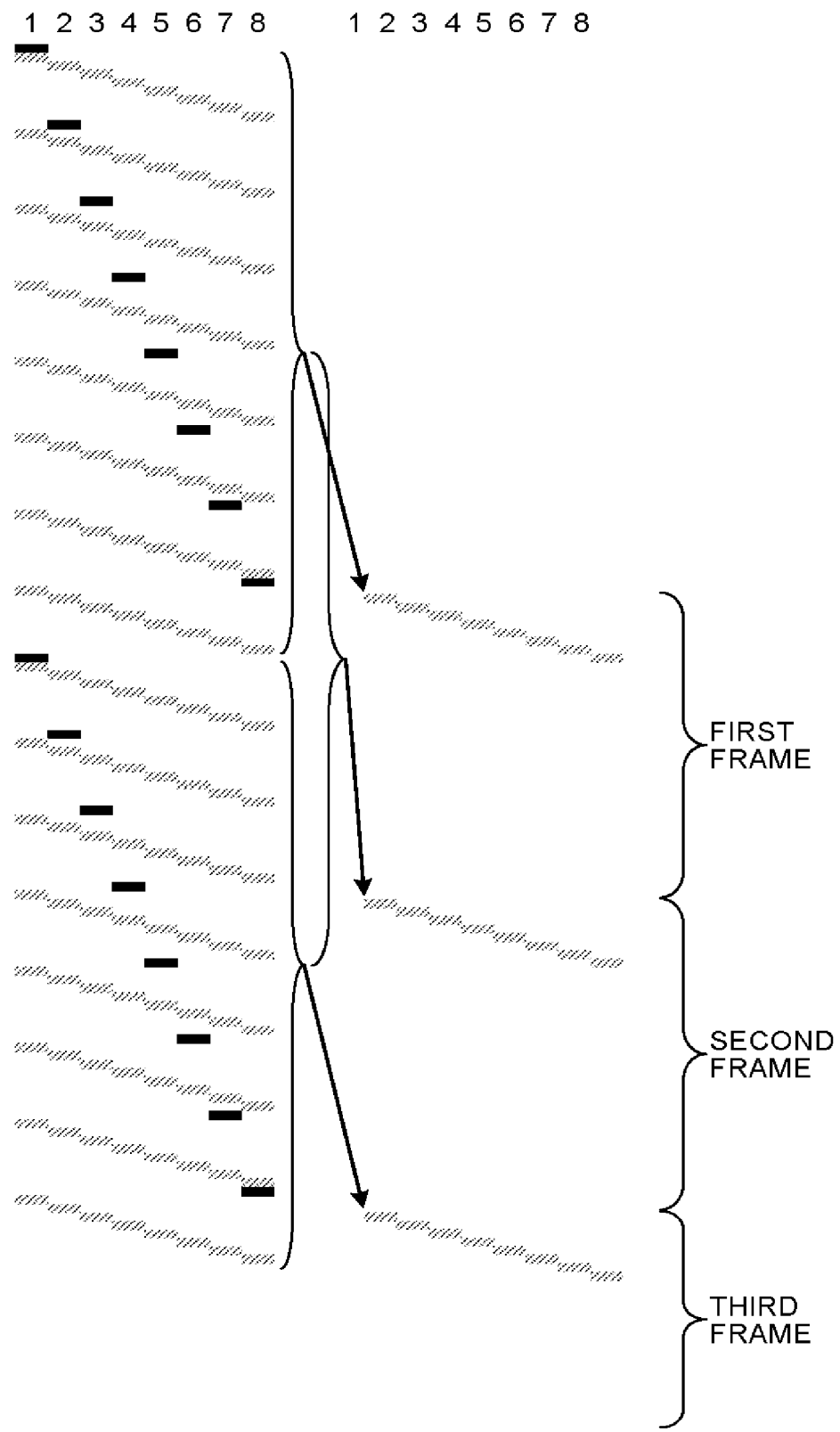
Figures 6, 7:
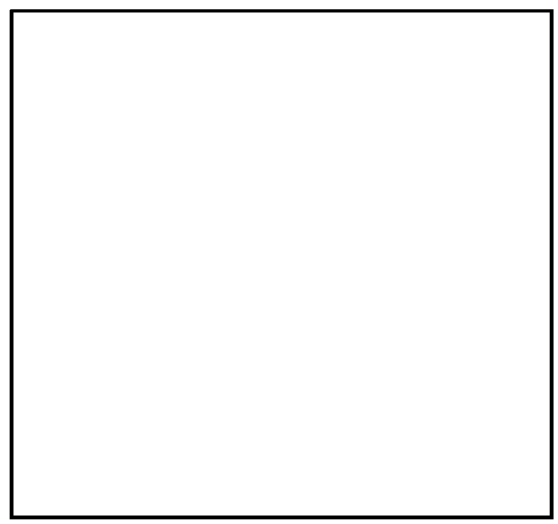
FIG. 7 and FIG. 8 are schematics for explaining the exemplary process of determining the rank to be reduced according to the first embodiment.

B-mode image data and Doppler image data can both be generated and displayed based on the reflection wave data collected with the high-frame-rate ultrasound scan. With this data, however, the B-mode image data cannot be generated and displayed using THI capable of achieving high image quality. The controlling circuitry 18 according to the first embodiment, therefore, performs the second ultrasound scan in a manner described below, in addition to the first ultrasound scan for the high-frame-rate imaging. FIGS. 4 to 6 are schematics of exemplary ultrasound scan according to the first embodiment.

The controlling circuitry 18 according to the first embodiment causes the ultrasound probe 1 to perform a run of the second ultrasound scan on one of a plurality of segments that are divisions of the second scanned region, between a plurality of runs of the first ultrasound scan, on the basis of time sharing. In other words, in the first embodiment, a part of the second ultrasound scan is performed between a plurality of runs of the first ultrasound scan, and the first ultrasound scan corresponding to several frames is completed in the time required for the entire second ultrasound scan corresponding to one frame to be completed. With such scan, the ultrasonic diagnostic apparatus according to the first embodiment can be specified with independent sets of ultrasonic wave transmission and reception conditions, for the first ultrasound scan and the second ultrasound scan, respectively. For example, the ultrasonic diagnostic apparatus according to the first embodiment can perform the second ultrasound scan using THI-based conditions. In other words, the second ultrasound scan can be executed using the ultrasonic wave transmission and reception conditions for THI that uses the filtering described above. The second ultrasound scan can then be executed using the ultrasonic wave transmission and reception conditions for THI that visualizes a moving image by transmitting ultrasonic waves at a plurality of rates along one scan line, e.g., AM imaging, PM imaging, AMPM imaging, and imaging using a differential component.

An example of the control process described above will now be explained with reference to FIG. 4. The controlling circuitry 18 divides second scanned region into four segments (first to fourth segments) based on an instruction from an operator, information provided as initial settings, or the like. "B" illustrated in FIG. 4 represents a segment scanned with transmission/reception conditions for B-mode imaging, and "D" illustrated in FIG. 4 represents a segment scanned with transmission/reception conditions for color-Doppler imaging. "D" illustrated in FIG. 4, for example, is a segment scanned in the high-frame-rate mode described above. In other words, in the first ultrasound scan illustrated in FIG. 4, an ultrasonic wave is transmitted and received once along each of the scan lines, instead of transmitting an ultrasonic wave in the same direction a plurality of number of times and receiving reflection waves a plurality of number of times, like in the general color Doppler imaging. As the first ultrasound scan, the controlling circuitry 18 controls to transmit and to receive an ultrasonic wave one time along each of the scan lines making up the first scanned region, and to acquire blood flow information from the reflection waves across a plurality of frames (high-frame-rate imaging).

To begin with, the controlling circuitry 18 controls to run the second ultrasound scan on the first segment (see (1) in FIG. 4), and to run the first ultrasound scan on the second scanned region (corresponding to one frame) (see (2) in FIG. 4). The controlling circuitry 18 then controls to run the second ultrasound scan on the second segment (see (3) in FIG. 4), and to run the first ultrasound scan on the second scanned region (corresponding to one frame) (see (4) in FIG. 4). The controlling circuitry 18 then controls to run the second ultrasound scan on the third segment (see (5) in FIG. 4), and to run the first ultrasound scan on the second scanned region (corresponding to one frame) (see (6) in FIG. 4). The controlling circuitry 18 then controls to run the second ultrasound scan on the fourth segment (see (7) in FIG. 4), and to run the first ultrasound scan on the second scanned region (corresponding to one frame) (see (8) in FIG. 4).

The controlling circuitry 18 runs the first ultrasound scan at an equal interval, as illustrated in FIG. 4. In other words, the controlling circuitry 18 controls to scan the same point "X" on a particular scan line in the first scanned region at constant interval "T", the scan point "X" being scanned once in each run of the first ultrasound scan (2), (4), (6), and (8) in FIG. 4. Specifically, the controlling circuitry 18 executes the first ultrasound scan at an equal interval by setting an equal time to each run of segmented scan in the second ultrasound scan. For example, the controlling circuitry 18 controls so that the same time is always required for each run of segmented scan (1), (3), (5), and (7) illustrated in FIG. 4 that is the second ultrasound scan. The controlling circuitry 18 uses the same conditions such as the size of the segments of the second scanned region, the number of scan lines, and the scan line density and depth. If the same number of scan lines is used in each run of segmented scan that is run as the second ultrasound scan, for example, the same time will be required for each run. The Doppler processing circuitry 14 performs a process described later to the data array ("$X_{n-3}$, $X_{n-2}$, $X_{n-1}$, $X_n$, . . . " illustrated in FIG. 4) acquired from the same position across the "D" frames, and outputs blood flow information for the point "X". With this approach, the scan of the entire second scanned region is completed in a time interval "4T", but the controlling circuitry 18 updates the tissue image data in units of one segment of the scanned region, instead of updating the tissue image data in units of the time interval "4T". Furthermore, when THI is performed based on the approach for visualizing a moving image by transmitting an ultrasonic wave at a plurality of rates along one scan line, the number of ultrasonic wave transmissions performed to acquire the received signals for one frame is increased. Therefore, compared with ordinary B-mode imaging or THI using filtering, the second scanned region needs to be divided into a larger number of segments. For example, for the PM imaging, the number of segments into which the second scanned region is divided is changed from four to eight. In such a case, scan of the entire second scanned region is completed at a time interval "8T". In such an example as well, the controlling circuitry 18 updates the tissue image data in units of one segment of the scanned region, instead of updating the tissue image data in units of the time interval "8T".

In the conventional color Doppler processing, because a data array enclosed as one packet is applied with the "MTI filtering process" and the "velocity/variance/power estimating process", the conventional color Doppler processing is only capable of outputting one piece of blood flow information for one packet. By contrast, in the color Doppler imaging using the high-frame-rate scan mode, there is no such a concept as a "packet" in the scan. Therefore, with the color Doppler processing performed in the high-frame-rate scan mode, the length of the data array used in outputting one piece of blood flow information can be changed to any length. Furthermore, with the color Doppler processing performed in the high-frame-rate scan mode, a data array used in the process of outputting blood flow information in a previous time phase may be used in a manner overlapping with the data array used in the subsequent time phase.

This overlapping use of data arrays will now be explained with reference to FIG. 5. Illustrated in FIG. 5 is an example in which the first scanned region is the same as the second scanned region, and the scanned region consists of eight scan lines from a first scan line to an eighth scan line. In FIG. 5, the eight scan lines are represented as "1, 2, 3, 4, 5, 6, 7, and 8", respectively, in the azimuth direction (in the direction in which the piezoelectric transducer elements are arranged in the ultrasound probe 1). In FIG. 5, the second ultrasound scan for the B-mode imaging is represented by a black rectangle, and the first ultrasound scan for Doppler mode imaging is represented by a hatched rectangle. FIG. 5 is a schematic illustrating how the scanned region illustrated in FIG. 2 is scanned in the scanning mode according to the first embodiment.

In the scan illustrated in FIG. 5, the second ultrasound scan is performed along the first scan line, and the first ultrasound scan is then performed sequentially along the first scan line to the eighth scan line. The second ultrasound scan is then performed along the second scan line, and the first ultrasound scan is then performed sequentially along the first scan line to the eighth scan line. In the scan illustrated in FIG. 5, the second ultrasound scan of the third scan line then performed, and the first ultrasound scan is then performed sequentially along the first scan line to the eighth scan line. The second ultrasound scan is then performed along the fourth scan line, and the first ultrasound scan is then performed sequentially along the first scan line to the eighth scan line.

In the scan illustrated in FIG. 5, the second ultrasound scan is then performed along the fifth scan line, and the first ultrasound scan is then performed sequentially along the first scan line to the eighth scan line. The second ultrasound scan is then performed along the sixth scan line, and the first ultrasound scan is then performed sequentially along the first scan line to the eighth scan line. In the scan illustrated in FIG. 5, the second ultrasound scan is then performed along the seventh scan line, and the first ultrasound scan is then performed sequentially along the first scan line to the eighth scan line. The second ultrasound scan is then performed along the eighth scan line, and the first ultrasound scan is then performed sequentially along the first scan line to the eighth scan line.

In the example illustrated in FIG. 5, the data array length is set to "8", and the number of overlapping data arrays between the frames to be displayed is set to "4". With such settings, as illustrated in FIG. 5, from the data collected from the first to eighth runs of the first ultrasound scan, Doppler data for the first frame is output, and the first frame of Doppler image data is generated and displayed. As illustrated in FIG. 5, Doppler data for the second frame is output, and the second frame of Doppler image data is generated and displayed, based on the data collected from the fifth to twelfth runs of the first ultrasound scan. As illustrated in FIG. 5, Doppler data for the third frame is output, and the third frame of Doppler image data is generated and displayed, based on the data collected from the ninth to sixteenth runs of the first ultrasound scan.

The second ultrasound scan for the B-mode imaging is completed at the timing at which the first ultrasound scan for two frames is completed, in the example illustrated in FIG. 5. In the example illustrated in FIG. 5, B-mode image data corresponding to a half of the scanned region (first scanned region) is updated while one frame of Doppler image data is displayed.

By using high-frame-rate ultrasound scan for the first ultrasound scan for the Doppler imaging, the scanned region (first scanned region) is not divided into a plurality of scan blocks between which a time lag is introduced, unlike the conventional technology. As a result, the entire scanned region can be ensured of temporal continuity without time lag, as illustrated in FIG. 6. Therefore, even with the processing of the Doppler processing circuitry 14 using the eigenvector MTI filter, which will be explained in detail, the ultrasonic diagnostic apparatus according to the first embodiment can generate and display Doppler image data with no abrupt change in the border.

The correlation matrix calculating circuitry 141 according to the first embodiment, to begin with, calculates a correlation matrix of the scanned region (first scanned region) from an array of reflection wave data acquired from the same position across a plurality of frames, the reflection wave data being collected by transmitting and receiving ultrasonic waves to the scanned region (first scanned region) consisting of a plurality of scan lines. Specifically, the correlation matrix calculating circuitry 141 according to the first embodiment uses an array of consecutive reflection wave data acquired from the same position, as a data array for calculating the correlation matrix of the scanned region, such an data array collected by repeating a scan in which the scan lines is switched across the scanned region (first scanned region) every time an ultrasonic wave is transmitted and received once. More specifically, the correlation matrix calculating circuitry 141 according to the first embodiment uses an array of consecutive reflection wave data acquired from the same position, as a data array for calculating the correlation matrix of the scanned region, such an data array being collected by repeating a scan in which an ultrasonic wave is transmitted and received once along each of the scan lines in the scanned region (first scanned region).

Specifically, the correlation matrix calculating circuitry 141 calculates a correlation matrix "$R_{xx}$" from following Expression (1).

$$R_{xx} = \frac{1}{M}\sum_{m=1}^{M} X_m X_m^H \tag{1}$$

"$x_m$" in Expression (1) is a representation of the data array at a position "m" as a column vector. The length "L" of the column vector "$x_m$" is the data length used in estimating the Doppler data (blood flow information) for one frame. For example, in the example illustrated in FIG. 5, "L" is "8". "$x_m^H$" in Expression (1) is a transpose matrix of the matrix representing the complex conjugate of each element in "$x_m$".

The position "m" herein is the position of a sampling point set in the total space in which the high-frame-rate ultrasound scan is performed. The position "m" is represented by a two-dimensional coordinate system when the scan is two dimensional, and by a three-dimensional coordinate system when the scan is three dimensional. "M" in Expression (1) is the total number of the positions "m".

In other words, the correlation matrix calculating circuitry 141 calculates the autocorrelation matrix of the data array corresponding to each of a plurality of sampling points based on Expression (1), and calculates the average of the autocorrelation matrixes for the respective sampling points. In this manner, the correlation matrix calculating circuitry 141 calculates the correlation matrix of the scanned region. The correlation matrix "$R_{xx}$" is a matrix with L rows by L columns, based on Expression (1). As described above, the data array length "L" from which the correlation matrix is calculated can be changed to any length. Furthermore, data arrays from which correlation matrixes are calculated can be used in an overlapping manner between the frames to be displayed.

The computing circuitry 142 then calculates a filter coefficient for suppressing the clutters resulting from the tissues by performing principal component analysis using the correlation matrix, and by performing a matrix operation for approximating and suppressing clutter components as a principal component. In the embodiment, the computing circuitry 142 calculates the eigenvalues of each of the correlation matrixes and eigenvectors corresponding to the respective eigenvalues. In other words, the computing circuitry 142 calculates "L" pairs of "an eigenvalue and an eigenvector" from the correlation matrix "$R_{xx}$". The computing circuitry 142 then establishes a matrix "V" by arranging the L eigenvectors in the order of eigenvalue size. The computing circuitry 142 calculates a matrix that is the matrix "V" having its rank reduced as a MTI filter matrix for suppressing clutter components. The computing circuitry 142 then calculates the MTI filter matrix "W" from Expression (2) below, by substituting "V" with a matrix in which the L eigenvectors are used as L column vectors, and in which the L column vectors are arranged in the descending order of eigenvalue size.

$$W = V \begin{pmatrix} 0 & & & & \\ & 0 & & & \\ & & \ddots & & \\ & & & 1 & \\ & & & & 1 \end{pmatrix} V^H \tag{2}$$

"$V^H$" in Expression (2) represents a conjugate transpose matrix of the matrix "V". The matrix positioned between "V" and "$V^H$" on the right-hand side of Expression (2) is a diagonal matrix with L rows and L columns. The resultant MTI filter matrix "W" has L rows and L columns, based on Expression (2). The number of principal components to be reduced, that is, the rank to be reduced is determined depending on how many diagonal elements are set to "zero" in the diagonal matrix with L rows and L columns. Hereinafter, the rank to be reduced is referred to as a "rank to be reduced".

A column vector (eigenvector) with a large eigenvalue corresponds to a clutter component having its frequency shifted by a smaller degree by Doppler shift, that is, a component moving slowly in the scanned region for the Doppler imaging. Expression (2) calculates a matrix resulting from reducing the rank of the matrix "V" by the rank to be reduced, by removing the components with larger eigenvalues, and inverse-transforms the matrix with "$V^H$". Expression (2) can achieve an MTI filter matrix "W" serving as a high-pass filter for removing the tissue movement component (clutter component).

The computing circuitry 142 determines the number of principal components to be reduced, that is the rank to be reduced, based on a preset value or a value designated by an operator, for example. It is however preferable for such a rank to be reduced to be determined adaptively based on the eigenvalue size when the scanned region includes some tissues moving at velocity that changes over time, due to heartbeats, for example, such as a heart or a blood vessel. In other words, the computing circuitry 142 changes the number of principal components reduced based on the eigenvalue size of the correlation matrixes. In the embodiment, the computing circuitry 142 changes the rank to be reduced based on the eigenvalue size.

Figure 8:
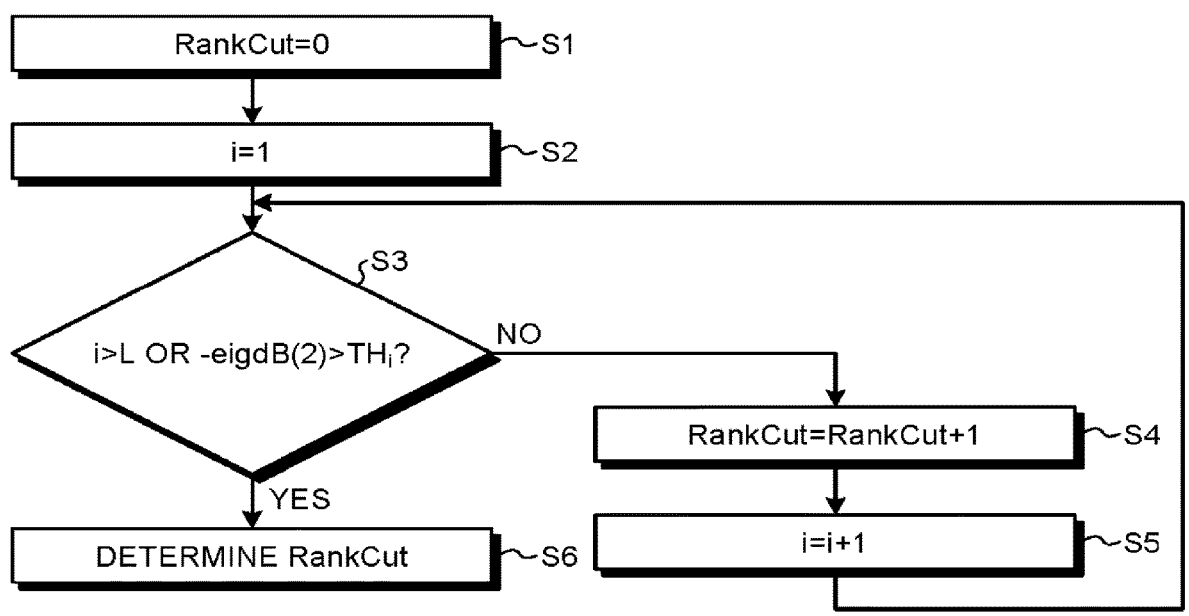

The logic for adaptively determining the rank to be reduced based on the eigenvalue size need to be optimized depending on the region where the ultrasound scan is performed. The computing circuitry 142 determines, for example, the rank to be reduced based on the threshold illustrated in FIG. 7 and the algorithm illustrated in FIG. 8. The algorithm illustrated in FIG. 8 determines the rank to be reduced based on the value resulting from dividing the second largest eigenvalue by the largest eigenvalue. FIGS. 7 and 8 are schematics for explaining an exemplary process of determining the rank to be reduced according to the first embodiment.

To begin with, the computing circuitry 142 defines the k-th eigenvalue among those in the correlation matrixes "$R_{xx}$" arranged in the descending order of the eigenvalue size as "eig(k)". "k" herein as an integer "1≤k≤L". The computing circuitry 142 then calculates a value "eigdB(k)" that is the k-th largest eigenvalue divided by the largest eigenvalue "eig(1)" from Expression (3) below, with "eigdB(k)" being represented in units of decibels.

$$\text{eigdB}(k)=10*\log_{10}(\text{abs}(\text{eig}(k))/\text{abs}(\text{eig}(1))) \quad (3)$$

In Expression (3), "abs" denotes a function for calculating the absolute value. In Expression (3), "eigdB(2)", where "k=2", is a value resulting from dividing the second largest eigenvalue by the largest eigenvalue "eig(1)", and represented in units of decibels.

Because acquired are L eigenvalues, the computing circuitry 142 uses L thresholds ($TH_i$, 1≤i≤L) for determining the rank to be reduced. To $TH_i$, a value varying depending on i is set. For example, when "L=8", eight thresholds "$TH_1$ to $TH_8$" are set in the manner illustrated in FIG. 7. In FIG. 7, $TH_1$ and $TH_2$ are set to "1000000 decibels". In FIG. 7, $TH_3$ is set to "20 decibels", and $TH_4$ is set to "15 decibels". In FIG. 7, $TH_5$ is set to "10 decibels", and $TH_6$ is set to "5 decibels". In FIG. 7, $TH_7$ and $TH_8$ are set to "−1 decibel". With the thresholds illustrated in FIG. 7, the rank to be reduced will be equal to or more than two and equal to or less than six, based on the algorithm illustrated in FIG. 8, which is explained later. In FIG. 8, "RankCut" denotes the rank to be reduced.

To begin with, the computing circuitry 142 sets "RankCut=0" (Step S1), and "i=1" (Step S2). The computing circuitry 142 determines whether "i" is larger than "L", and "−eigdB(2)" is larger than "$TH_i$" (Step S3). If "i" is equal to or less than "L", and "−eigdB(2)" is equal to or less than "$TH_i$" (NO at Step S3), the computing circuitry 142 increments the rank to be reduced, and sets "RankCut=RankCut+1" (Step S4).

The computing circuitry 142 sets "i=i+1" (Step S5), and performs the determination at Step S3. "−eigdB(2)" used in the determination at Step S3 subsequent to the first Step S5 is a value resulting from, for example, multiplying "−1" to the quotient of the second largest eigenvalue divided by the largest eigenvalue "eig(1)", "eig(1)" being the largest eigenvalue in a matrix with the largest eigenvalue removed from a matrix of the L eigenvalues arranged in the descending order of eigenvalue size, and "−eigdB(2)" being represented in units of decibels.

If "i" is larger than "L", or if "−eigdB(2)" is larger than "$TH_i$" (YES at Step S3), the computing circuitry 142 determines the latest "RankCut" as the rank to be reduced (Step S6).

As the algorithm for adaptively determining the rank to be reduced based on the eigenvalue size, various algorithms other than that described above may be used. Such an algorithm may be selected based on the region where the ultrasound image is captured, for example.

The computing circuitry 142 determines the rank to be reduced for each of the frames to be displayed using the algorithm illustrated in FIG. 8, and calculates the MTI filter matrix "W".

The MTI filter processing circuitry 143 outputs a data array representing the extraction of blood flow signals acquired from blood flows, with clutter components suppressed, from an array of consecutive reflection wave data acquired from the same position (the same sampling point), using the filter coefficient. In the embodiment, the MTI filter processing circuitry 143 outputs a data array representing the extraction of blood flow signals acquired from the blood flows, with clutter components suppressed, from an array of consecutive reflection wave data acquired from the same position (the same sampling point), using the filter matrix. Specifically, using the column vector "$x_m$" acquired from the position "m" as input data, the MTI filter processing circuitry 143 calculates a column vector "$y_m$" that is output data for the position "m", based on Expression (4) below, using the input data and the MTI filter matrix "W". The length of the column vector "$y_m$" is herein "L".

$$y_m = W x_m \quad (4)$$

The MTI filter processing circuitry 143 calculates Expression (4) for each of the "M" sampling points. As a result, the MTI filter processing circuitry 143 outputs a piece of output data for each of the "M" sampling points to the estimating circuitry 144.

The estimating circuitry 144 then performs the autocorrelation computing process and the velocity/variance/power estimating process to the column vector "$y_m$" that is the output data for the position "m", to estimate blood flow information for the position "m" thereby. To begin with, the estimating circuitry 144 computes an autocorrelation value between lag 0 and lag 1 from the column vector "$y_m$". Denoting the lag 0 by "$C_0$" and the lag 1 by "$C_1$", the estimating circuitry 144 calculates the lag 0 "$C_0$" from Expression (5) below, and calculates the lag 1 "$C_1$" from Expression (6) below.

$$C_0 = \frac{1}{L}\sum_{i=1}^{L} |Y_i|^2 \qquad (5)$$

$$C_1 = \frac{1}{L-1}\sum_{i=1}^{L-1} Y_i^* Y_{i+1} \qquad (6)$$

In Expressions (5) and (6), the subscript "m" representing the position in the column vector "$y_m$" is omitted, and the number of elements "i" in the column vector "$y_m$" is provided as a subscript. In Expression (6), the superscript asterisk "*" represents complex conjugation. The estimating circuitry 144 calculates "$C_0$" and "$C_1$" for each of the "M" sampling points.

The estimating circuitry 144 calculates velocity "V" from "$C_0$" and "$C_1$" based on Expression (7) below, calculates variance "T" from "$C_0$" and "$C_1$" based on Expression (8) below, and calculates power "P" from "$C_0$" based on Expression (9) below.

$$V = a\tan2(\text{imag}(c_1), \text{real}(c_1)) \qquad (7)$$

$$T = 1 - \frac{|c_1|}{c_0} \qquad (8)$$

$$P = 10\log_{10}(c_0) \qquad (9)$$

In Expression (7), "a tan 2" denotes an "arc tangent function" for outputting an angle ranging from "$-\pi$ to $+\pi$", "imag" is a function for outputting only the imaginary part of the complex number, and "real" is a function for outputting the real part of the complex number. The power is acquired as lag 0 from the autocorrelation operation, and the velocity and the variance are acquired by frequency-analyzing the result of the autocorrelation operation.

The estimating circuitry 144 calculates "V, T, and P" for each of the "M" sampling points. The estimating circuitry 144 then outputs "V, T, and P" for all of the "M" sampling points to the image generating circuitry 15, as a piece of Doppler data corresponding to one frame.

The image generating circuitry 15 then generates ultrasound image data (color Doppler image data) from the blood flow information (Doppler data) estimated using the filter coefficient. In the embodiment, the image generating circuitry 15 generates ultrasound image data (color Doppler image data), from the blood flow information (Doppler data) estimated using the MTI filtering matrix. The controlling circuitry 18 then displays the ultrasound image data (color Doppler image data) onto the display 2.

Figure 9:
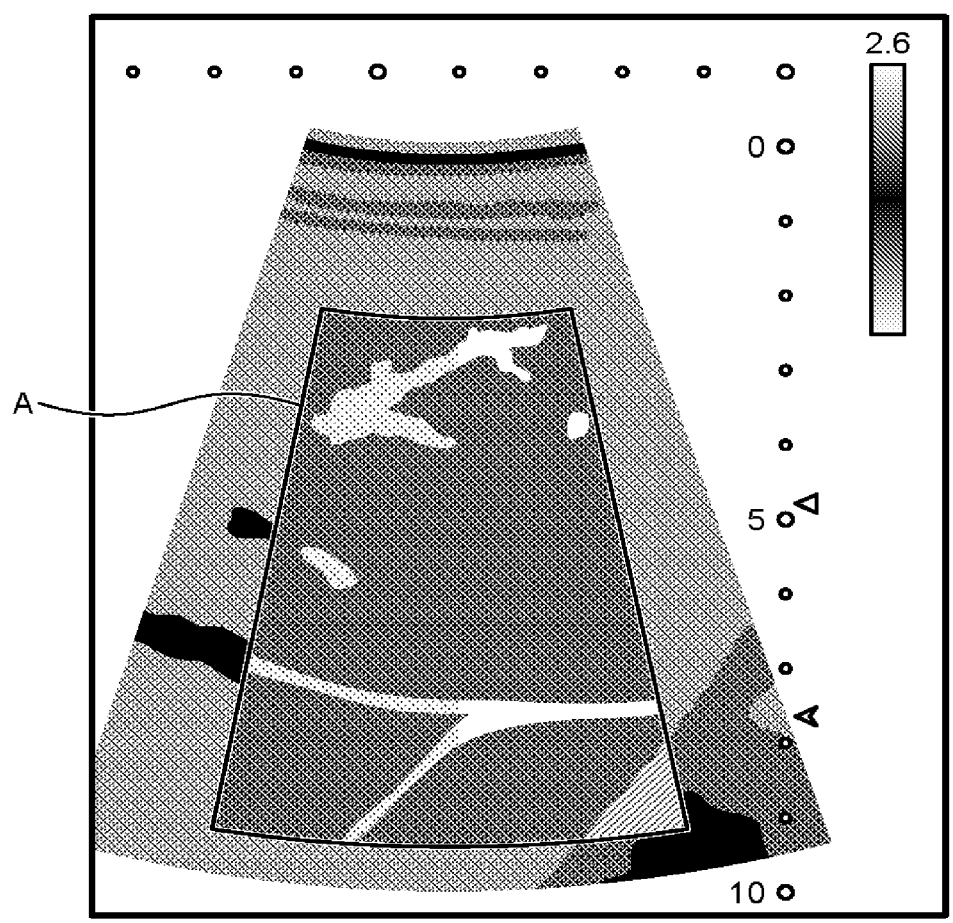
FIG. 9 is a schematic illustrating an exemplary image data displayed using the conventional technology.
Figure 10:
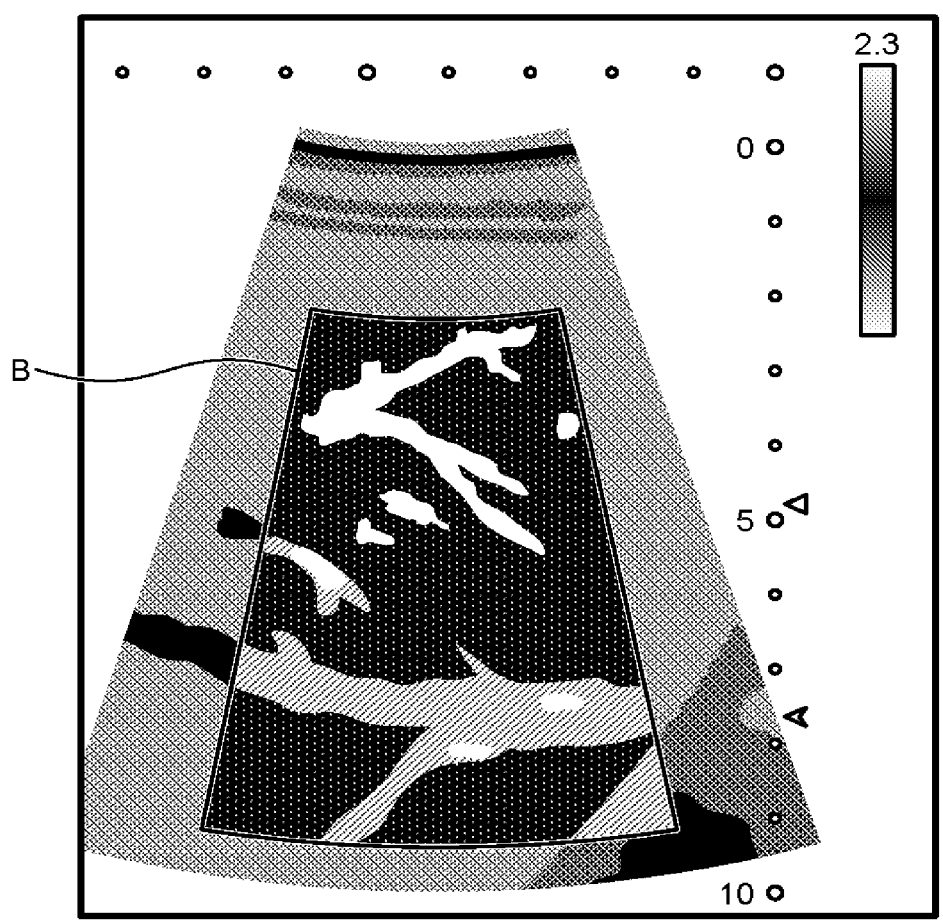
FIG. 10 is a schematic illustrating an exemplary image data displayed in the first embodiment.

FIG. 9 is a schematic illustrating an exemplary image data displayed using the conventional technology. FIG. 10 is a schematic illustrating an exemplary image data displayed in the first embodiment. The color Doppler image data A illustrated in FIG. 9 is image data generated and displayed using the high-frame-rate ultrasound scan and a polynomial regression filter. The color Doppler image data B illustrated in FIG. 10 is image data generated and displayed using the high-frame-rate ultrasound scan and the eigenvector MTI filter calculated with the rank to be reduced that is determined adaptively based on the eigenvalue size.

In the color Doppler image data A illustrated in FIG. 9, blood flows are represented with some noise, that is, in low contrast. By contrast, in the color Doppler image data B illustrated in FIG. 10, blood flows are represented without any noise, that is, in high contrast. Small blood flows not represented in the color Doppler image data A illustrated in FIG. 9 are clearly represented in the color Doppler image data B illustrated in FIG. 10. In the color Doppler image data B illustrated in FIG. 10, no abrupt border is shown because the high-frame-rate ultrasound scan is used.

By using the eigenvector MTI filter calculated with the rank to be reduced that is adaptively determined based on the eigenvalue size, the characteristics of the MTI filter calculated in the first embodiment are changed accordingly to the tissue movements. As a result, in the blood flow image data generated and displayed in the first embodiment, motion artifacts are reduced dramatically.

When an IIR filter or a polynomial regression filter is used in the high-frame-rate mode, for example, such a filter tends to pass clutter signals more easily, and motion artifacts may be produced. To address this issue, correction or the like is sometimes performed to lower the blood flow information values based on the average power in a plurality of frames. While such correction can reduce the motion artifacts, sometimes blood flow information may be temporarily unrepresented when the ultrasound probe 1 is moved, for example. By contrast, because the motion artifacts are reduced dramatically in the first embodiment, such correction is not required.

Figure 11:
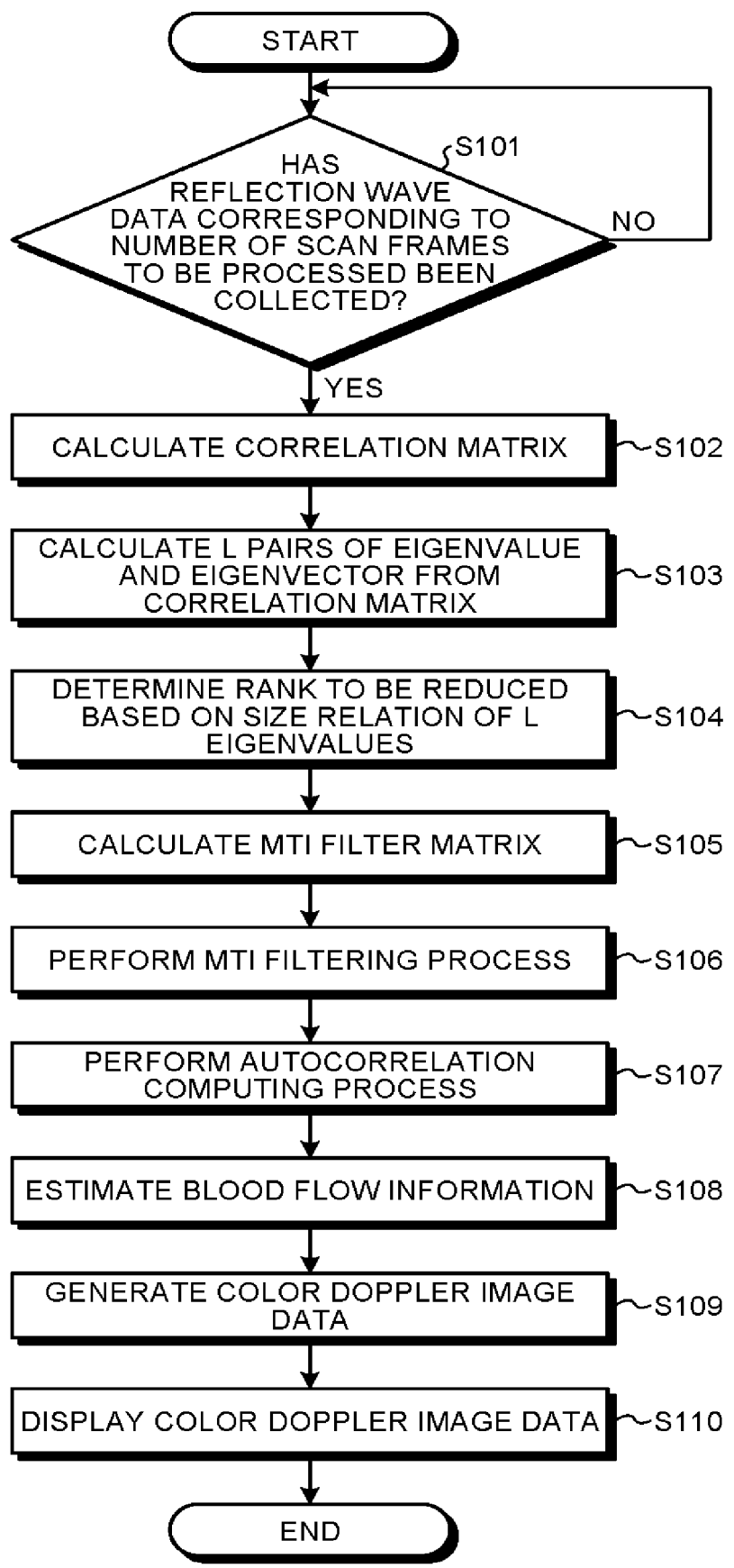
FIG. 11 is a flowchart for explaining an exemplary process performed by the ultrasonic diagnostic apparatus according to the first embodiment.

An exemplary process performed by the ultrasonic diagnostic apparatus according to the first embodiment will now be explained with reference to FIG. 11. FIG. 11 is a flowchart for explaining an exemplary process performed by the ultrasonic diagnostic apparatus according to the first embodiment. The flowchart illustrated in FIG. 11 explains the process of generating and displaying Doppler image data performed by the ultrasonic diagnostic apparatus according to the first embodiment.

As illustrated in FIG. 11, the controlling circuitry 18 in the ultrasonic diagnostic apparatus according to the first embodiment determines whether reflection wave data corresponding to the number of scan frames to be processed (corresponding to the data length) has been collected (Step S101). If reflection wave data corresponding to the number of scan frames has not been collected yet (NO at Step S101), the controlling circuitry 18 waits until the data is collected.

If reflection wave data corresponding to the number of scan frames has been collected (YES at Step S101), the correlation matrix calculating circuitry 141 calculates the correlation matrix of the scanned region based on an instruction from the controlling circuitry 18 (Step S102), and the computing circuitry 142 calculates L pairs of an eigenvalue and an eigenvector from the correlation matrix (Step S103).

The computing circuitry 142 then determines the rank to be reduced based on the size relation among the L eigenvalues (Step S104), and calculates an MTI filter matrix (Step S105). The MTI filter processing circuitry 143 then performs the MTI filtering process (Step S106), and the estimating circuitry 144 performs the autocorrelation computing process using the output data output from the MTI filtering process (Step S107). The estimating circuitry 144 then estimates the blood flow information from the result of the autocorrelation computing process (Step S108).

The image generating circuitry 15 then generates color Doppler image data based on the blood flow information (Step S109). The display 2 then displays the color Doppler image data under the control of the controlling circuitry 18 (Step S110), and the process is ended.

As described above, according to the first embodiment, in addition to the high-frame-rate ultrasound scan, the blood flow information is estimated using the eigenvector MTI filter. Therefore, in the first embodiment, one correlation matrix can be calculated for the entire scanned region, and the entire image can be applied with the same eigenvector MTI filtering. The resultant Doppler image data therefore has no abrupt border resulting from the difference in the MTI filter characteristics. Furthermore, because there is no scan block resulting from alternating scan used in the conventional CFM, the image has no abrupt border resulting from the scan blocks. Therefore, according to the first embodiment, the image quality of an image visualized from the blood flow information can be improved using the adaptive MTI filtering using eigenvectors.

Furthermore, according to the first embodiment, because the high-frame-rate ultrasound scan is used, the length of data arrays to be processed can be changed to any length. By extending the data array length to be used, the image quality of the Doppler image data can be improved. Furthermore, according to the first embodiment, because the high-frame-rate ultrasound scan is used, a data array to be processed can be set among a plurality of frames to be displayed in an overlapping manner. The frame rate for displaying Doppler image data can therefore be improved.

Furthermore, according to the first embodiment, because an eigenvector MTI filter adaptively calculated using the rank to be reduced determined based on the eigenvalue size, the MTI filter characteristics can be changed accordingly to the tissue movements. As a result, according to the first embodiment, motion artifacts can be reduced dramatically.

Explained above is an example in which segmented scan, explained with reference to FIGS. 4 and 5, is used for the B-mode ultrasound scan. However, the first embodiment may be used in any configuration using any type of B-mode ultrasound scan.

Second Embodiment

Explained now in a second embodiment is a technique for further improving the image quality of the Doppler image data generated using the eigenvector MTI filter.

An ultrasonic diagnostic apparatus according to the second embodiment has the same configuration as the ultrasonic diagnostic apparatus according to the first embodiment explained with reference to FIG. 1. The Doppler processing circuitry 14 according to the second embodiment, however, calculates the MTI filter matrix following the process explained below.

In the first embodiment, one correlation matrix is calculated for the entire scanned region including the blood flows to be displayed, and the same MTI filter is applied to the entire image. When tissue movements vary greatly depending on where the tissue is found in the scanned region including the blood flows to be displayed, it is preferable for the scanned region to be divided into a plurality of processing blocks, and for an eigenvector MTI filter to be calculated for each of the processing blocks, so that the optimal MTI filtering is performed to each of the processing blocks. In such a case, however, the resultant Doppler image data may have abrupt borders between the processing blocks, due to the characteristics difference of the filters.

To address this issue, in the second embodiment, the coefficient for the eigenvector MTI filter is calculated by specially interpolating the correlation matrixes calculated for the respective processing blocks. In the second embodiment, ultrasound scan is performed in the same manner as the high-frame-rate ultrasound scan explained in the first embodiment.

To begin with, the correlation matrix calculating circuitry 141 according to the second embodiment calculates a correlation matrix of each of a plurality of sections that is divisions of the scanned region (a plurality of processing blocks). The correlation matrix calculating circuitry 141 then calculates a correlation matrix of each of a plurality of segmented sections that are segments of each of the processing blocks (a plurality of segmented processing blocks), by performing interpolation using the correlation matrixes for the respective processing blocks.

The computing circuitry 142 according to the second embodiment then calculates a filter coefficient for each of the segmented processing blocks from the correlation matrix of the corresponding segmented processing block. Specifically, the computing circuitry 142 calculates a filter matrix for each of the segmented processing blocks from the correlation matrix of the corresponding segmented processing block. The MTI filter processing circuitry 143 according to the second embodiment then extracts a blood flow signal for each of the sampling points using the filter coefficient for the corresponding segmented processing block. Specifically, the MTI filter processing circuitry 143 extracts a blood flow signal received from each of the sampling points, using the filter matrix for the corresponding segmented processing block. The estimating circuitry 144 according to the second embodiment then estimates the blood flow information at the corresponding sampling point. The image generating circuitry 15 generates ultrasound image data (Doppler image data) from the blood flow information estimated using the filter coefficients for the respective segmented processing blocks. Specifically, the image generating circuitry 15 generates ultrasound image data (Doppler image data) from the blood flow information estimated using filter matrixes for the respective segmented processing blocks.

Figure 12:
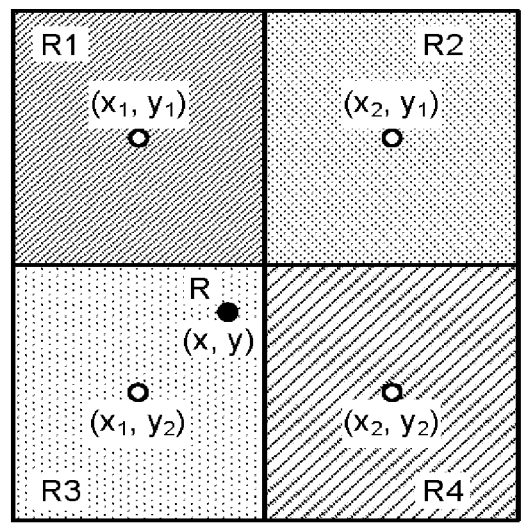
FIG. 12 is a schematic illustrating an exemplary process performed by correlation matrix calculating circuitry according to a second embodiment.

FIG. 12 is a schematic illustrating an exemplary process performed by the correlation matrix calculating circuitry according to the second embodiment. For example, the scanned region is divided into four processing blocks (R1, R2, R3, and R4), as illustrated in FIG. 12. The number in which the scanned region is divided and how the processing blocks are established can be specified in any way. The correlation matrix calculating circuitry 141 performs the calculating using Expression (1) as explained in the first embodiment in each of the processing blocks R1 to R4. Through this process, the correlation matrix calculating circuitry 141 calculates a correlation matrix "$R_1$" for the processing block R1, a correlation matrix "$R_2$" for the processing block R2, a correlation matrix "$R_3$" for the processing block R3, and a correlation matrix "$R_4$" for the processing block R4. In this example, the central coordinates of the processing block R1 is ($x_1$, $y_1$); the central coordinates of the processing block R2 is ($x_2$, $y_1$); the central coordinates of the processing block R3 is ($x_1$, $y_2$); and the central coordinates of the processing block R4 is ($x_2$, $y_2$), as illustrated in FIG. 12.

When each of the segmented processing blocks are established as individual sampling points in the scanned region, for example, the correlation matrix calculating circuitry 141 calculates the correlation matrix of a sampling point R(x,y) by means of bilinear interpolation using Expression (10) below.

$$R = \frac{R_1(x_2 - x)(y_2 - y) + R_2(x - x_1)(y_2 - y) + R_3(x_2 - x)(y - y_1) + R_4(x - x_1)(y - y_1)}{(x_2 - x_1)(y_2 - y_1)} \quad (10)$$

The computing circuitry 142 then calculates MTI filter matrixes for respective M sampling points from Expression (2), using the correlation matrixes for the respective M sampling points. The computing circuitry 142 determines the rank to be reduced for each of the M sampling points based on the eigenvalue size. The filter processing circuitry 143 then extracts the blood flow signal corresponding to each of the sampling points using the corresponding MTI filter matrix, and the estimating circuitry 144 estimates the blood flow information at the corresponding sampling point.

Figure 13:
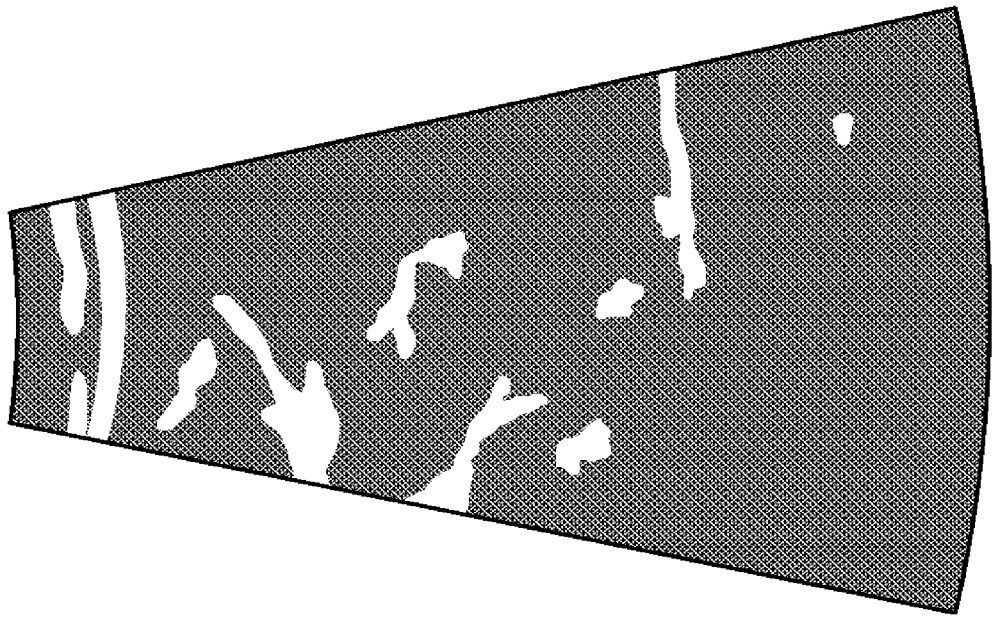
FIG. 13 is a schematic for explaining the effect of the second embodiment.
Figure 13:
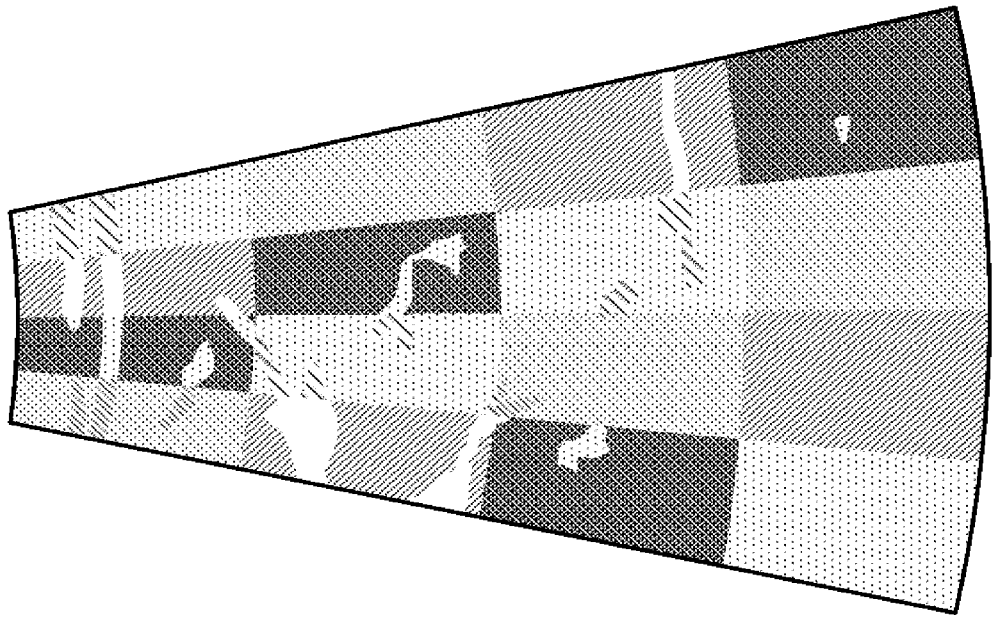

FIG. 13 is a schematic for explaining the effect of the second embodiment. The left schematic illustrated in FIG. 13 is Doppler image data displayed by dividing the scanned region including the blood flows to be displayed into 16 processing blocks, and calculating an MTI filter matrix for each of the processing blocks. The right schematic illustrated in FIG. 13 is Doppler image data displayed by dividing the scanned region including the blood flows to be displayed into 16 processing blocks, calculating a correlation matrix of each of the sampling points by interpolation, and calculating an MTI filter matrix for each of the sampling points.

As illustrated in the left schematic in FIG. 13, the Doppler image data resultant of the process without the interpolation presents abrupt borders between the 16 processing blocks. By contrast, the Doppler image data resultant of the process with the interpolation has no abrupt border between the 16 processing blocks, as illustrated in the right schematic in FIG. 13.

Although explained above is an example in which one segmented processing block is established as one sampling point, the second embodiment may also be implemented to divide the scanned region into a plurality of segmented processing blocks each having 10 sampling points, for example, and to calculate an MTI filter matrix for each of such segmented processing blocks, so that the processing load is reduced.

Figure 14:
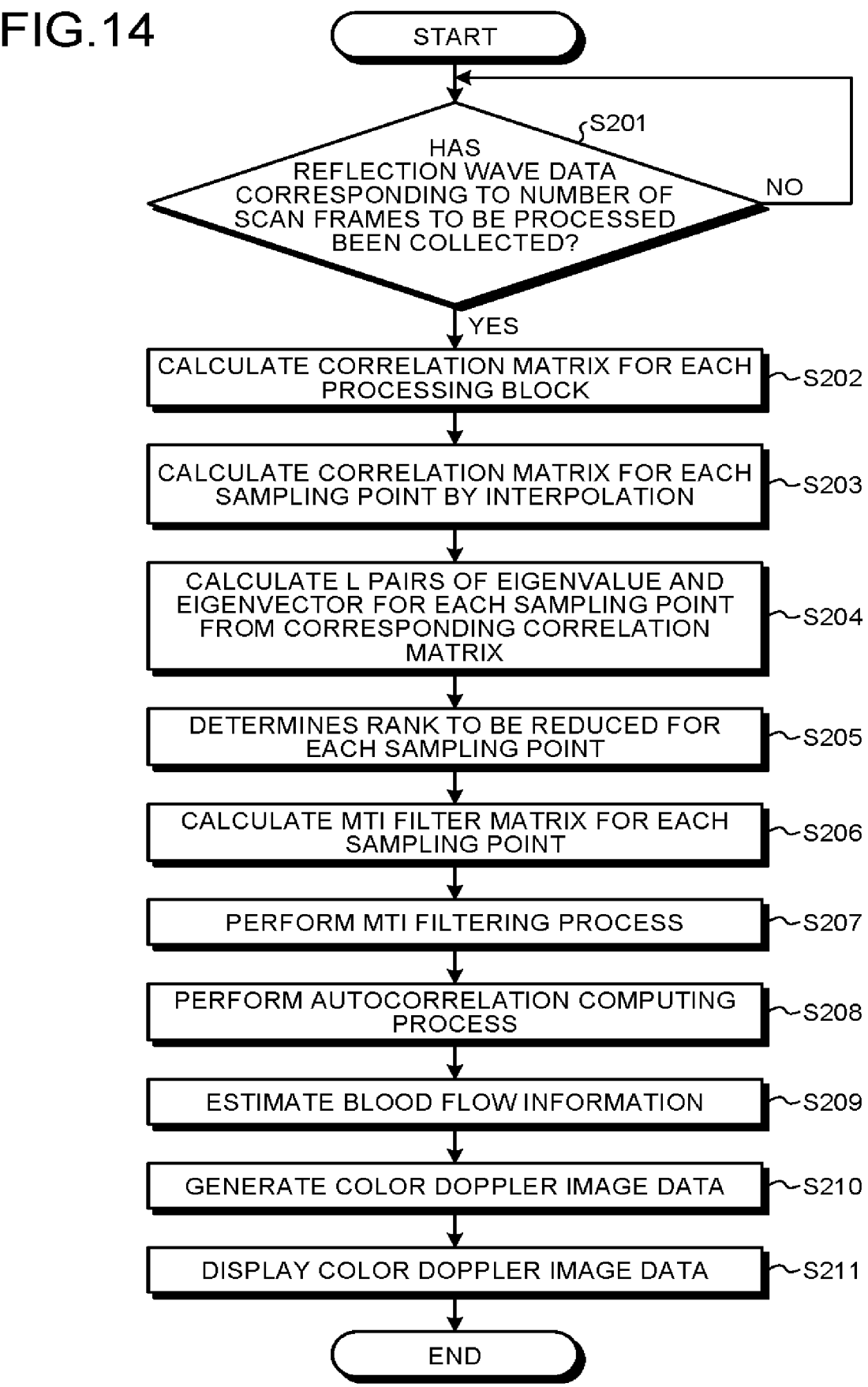
FIG. 14 is a flowchart for explaining an exemplary process performed by an ultrasonic diagnostic apparatus according to the second embodiment.

An exemplary process performed by the ultrasonic diagnostic apparatus according to the second embodiment will now be explained with reference to FIG. 14. FIG. 14 is a flowchart for explaining an exemplary process performed by the ultrasonic diagnostic apparatus according to the second embodiment. The flowchart illustrated in FIG. 14 explains the process of generating and displaying Doppler image data performed by the ultrasonic diagnostic apparatus according to the second embodiment. Furthermore, illustrated in FIG. 14 is an example in which the segmented processing block is established as one sampling point.

As illustrated in FIG. 14, the controlling circuitry 18 in the ultrasonic diagnostic apparatus according to the second embodiment determines whether reflection wave data corresponding to the number of scan frames to be processed (corresponding to the data length) has been collected (Step S201). If reflection wave data corresponding to the number of scan frames has not been collected yet (NO at Step S201), the controlling circuitry 18 waits until the data is collected.

If reflection wave data corresponding to the number of scan frames has been collected (YES at Step S201), the correlation matrix calculating circuitry 141 calculates a correlation matrix of each of the processing blocks based on an instruction from the controlling circuitry 18 (Step S202), and calculates a correlation matrix of each of the sampling points by interpolation (Step S203). The computing circuitry 142 calculates L pairs of an eigenvalue and an eigenvector for each of the sampling points from the corresponding correlation matrix (Step S204).

The computing circuitry 142 then determines the rank to be reduced for each of the sampling points (Step S205), and calculates an MTI filter matrix for each of the sampling points (Step S206). The MTI filter processing circuitry 143 then performs the MTI filtering process (Step S207), and the estimating circuitry 144 performs the autocorrelation computing process using the data output from the MTI filtering process (Step S208). The estimating circuitry 144 then estimates the blood flow information from the result of the autocorrelation computing process (Step S209).

The image generating circuitry 15 then generates color Doppler image data from the blood flow information (Step S210). The display 2 then displays the color Doppler image data under the control of the controlling circuitry 18 (Step S211), and the process is ended.

As described above, in the second embodiment, by calculating a correlation matrix for each of the segmented processing blocks by the interpolation using the correlation matrixes for the respective processing blocks, an MTI filter matrix optimal for each of the segmented processing blocks can be calculated. As a result, in the second embodiment, Doppler image data with motion artifacts dramatically reduced can be generated and displayed even when tissue movements vary greatly depending on where the tissue is.

With the interpolation explained in the second embodiment, the first ultrasound scan for the Doppler imaging may not be the high-frame-rate ultrasound scan. In other words, the first ultrasound scan according to the second embodiment may be any scan as long as an array of reflection wave data capable of estimating blood flow information can be collected. For example, even with the alternating scan, the interpolation explained in the second embodiment can reduce the artifacts resulting from the scan blocks and the processing blocks dramatically.

In such a case, the correlation matrix calculating circuitry 141 divides the scanned region, which is scanned by transmitting and receiving ultrasonic waves in some kind of scan mode, into a plurality of processing blocks, and calculates a correlation matrix of each of the processing blocks, from an array of reflection wave data collected from the same position across the different blocks. The correlation matrix calculating circuitry 141 then calculates correlation matrixes for a plurality of respective segmented processing blocks by performing the interpolation using the correlation matrixes for the respective processing blocks. The computing circuitry 142 then calculates a filter coefficient for suppressing clutters resulting from the tissues, for each of the segmented sections. The computing circuitry 142 calculates such a filter coefficient by performing principal component analysis using a correlation matrix on the corresponding segmented section, and performing a matrix operation that approximates and reduces the clutter components as a principal component. Specifically, the computing circuitry 142 calculates eigenvalues of the corresponding correlation matrix and eigenvectors corresponding to the respective eigenvalues for each of the segmented processing blocks, and calculates a matrix achieved by reducing the rank of a matrix consisting of an arrangement of the eigenvectors arranged in the order of the eigenvalue size, as the MTI filter matrix for suppressing the clutter components. In this manner, the computing circuitry 142 calculates the filter matrix for each of a plurality of segmented processing blocks.

Third Embodiment

Figure 15:
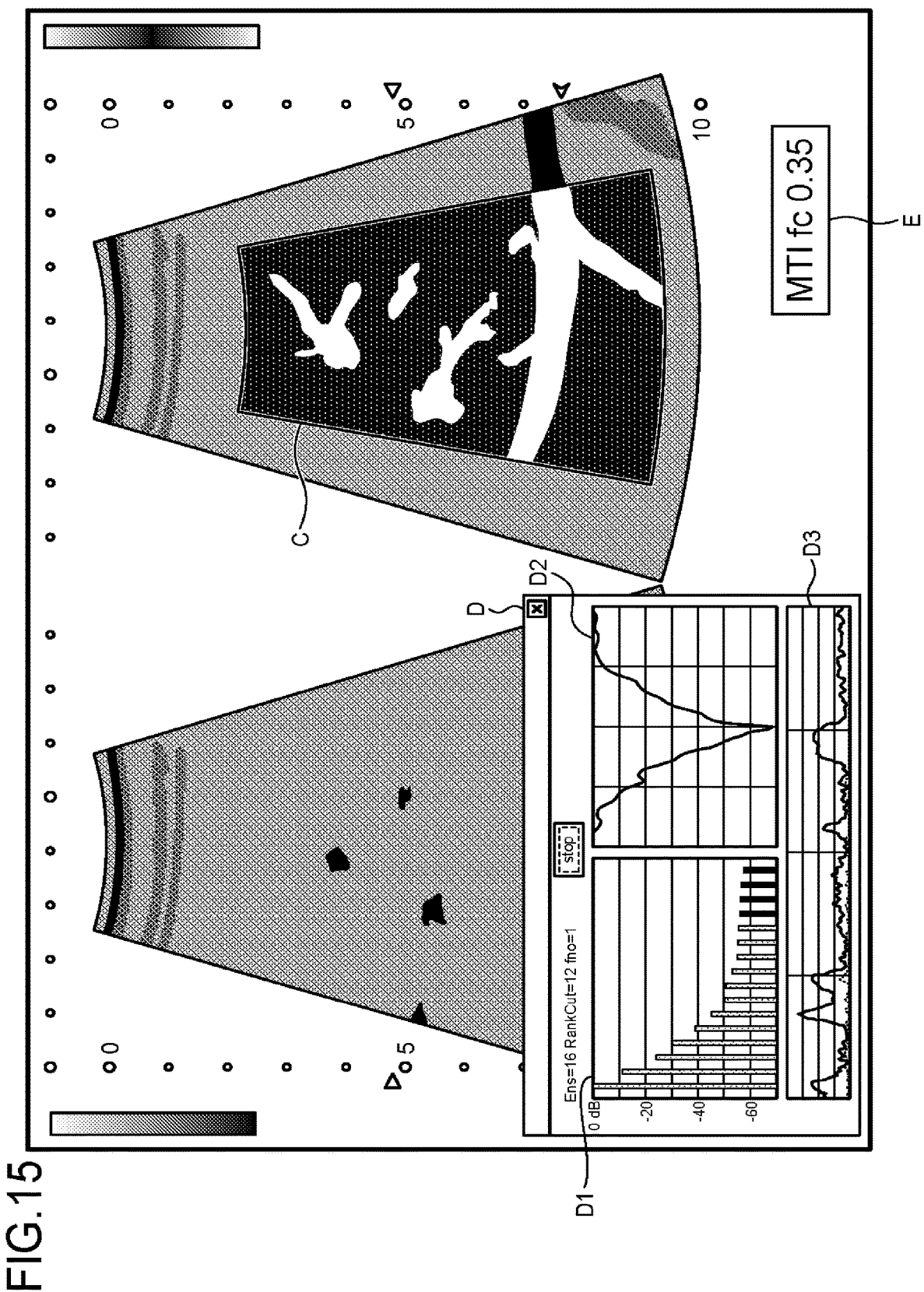
FIG. 15 is a schematic for explaining a third embodiment.

Explained in a third embodiment with reference to FIG. 15 is an example in which the filter coefficient, that is, the information used in calculating the MTI filter matrix, is output while the process explained in the first or the second embodiment is being executed. FIG. 15 is a schematic for explaining the third embodiment.

As described earlier, calculated in the process explained in the first embodiment is an MTI filter matrix optimized for the tissue movements in the entire scanned region, and calculated in the process explained in the second embodiment is an MTI filter matrix optimized for the tissue movements in each of the segmented processing blocks. The information used in calculating the MTI filter matrix is updated in units of one frame in the first embodiment, and is updated in units of a segmented processing block in each of the frames in the second embodiment. Because such information serves as diagnostic information visualizing the tissue movements, controlling to output such information, e.g., to display, to store in a storage medium, or to print out, serves to provide useful information to the operators.

The controlling circuitry 18 according to the third embodiment therefore controls to output the information related to the filter coefficient. Specified as the information related to the filter coefficient is at least one of the information related to the eigenvalues used in calculating the filter coefficient, the frequency characteristics of the filter coefficient, the cutoff frequency of the filter coefficient, and the power input to and output from the filter coefficient. Specifically, the controlling circuitry 18 controls to output information related to the MTI filter matrix. Specified as the information related to the MTI filter matrix is at least one of the information related to the eigenvalues used in calculating the MTI filter matrix, the frequency characteristics of the MTI filter matrix, the cutoff frequency of the MTI filter matrix, and the power input to and output from the MTI filter matrix.

For example, under the control of the controlling circuitry 18, the display 2 displays the information related to the MTI filter matrix used in generating Doppler image data C that is the current frame, in an area D and an area E, as illustrated in FIG. 15. The Doppler image data C is a piece of blood flow image generated and displayed as a result of the process explained in the first embodiment.

As illustrated in FIG. 15, the display 2 displays the information related to the eigenvalues used in calculating the MTI filter matrix in the subarea D1 in the area D. "Ens=16" displayed in the subarea D1 indicates that the data length is 16. "fno=1" indicates that the Doppler image data C is the first frame. "RankCut=12" displayed in the subarea D1 indicates that the rank to be reduced is 12. In other words, "RankCut=12" indicates that having been used is an MTI matrix acquired by removing the eigenvectors corresponding to the top 12 eigenvalues out of the 16 eigenvalues.

The subarea D1 in the area D displays the 16 eigenvalues as a bar chart, as illustrated in FIG. 15. In the bar chart illustrated in FIG. 15, the 16 eigenvalues calculated from the correlation matrix are plotted in the descending order of the eigenvalue size. In the bar chart illustrated in FIG. 15, using the largest one of the 16 eigenvalues to "zero decibels," the second to the sixteenth eigenvalues are converted into units of decibels. The controlling circuitry 18 calculates the decibels of the "k-th" eigenvalue from Expression (11) below.

$$10\log_{10}\frac{|eig(k)|}{|eig(1)|} \tag{11}$$

In the bar chart illustrated in FIG. 15, the 12 bars filled with dots represents eigenvalues having been removed as the tissues components, and the four black bars represent eigenvalues displayed as the blood flow component. The bar chart displayed in the subarea D1 is updated every time the frame is updated.

The display 2 also displays the frequency characteristics of the MTI filter matrix "W" in the subarea D2 in the area D, as illustrated in FIG. 15. For example, the controlling circuitry 18 controls to display a line chart representing the frequency characteristics of the MTI filter matrix "W" in decibels in the subarea D2. The controlling circuitry 18 calculates the decibels representing the frequency characteristics based on Expression (12) below.

$$H(f) = 10\log_{10}\left(\frac{1}{L}\sum_{i=1}^{L}\left|\sum_{k=1}^{L}W_{i,k}e^{-j2\pi f(k-1)}\right|^2\right)(-0.5 \le f \le 0.5) \tag{12}$$

The line chart of the frequency characteristics displayed in the subarea D2 is updated every time the frame is updated.

The display 2 also displays the cutoff frequency of the MTI filter matrix "W" in the area E, as illustrated in FIG. 15. "MTI fc 0.35" in the area E indicates that the cutoff frequency resulting in "−20 decibels" in the MTI filter matrix for the first frame is "0.35". The controlling circuitry 18 calculates the cutoff frequency resulting in "−20 decibels" from Expression (13) below.

((Frequency resulting in −20 decibels at positive frequency)−(Frequencyresulting in −20 decibels at negativefrequency))/2 (13)

The cutoff frequency displayed in the area E is updated every time the frame is updated.

The display 2 also displays the power input to and output from the MTI filter matrix in the subarea D3 in the area D, as illustrated in FIG. 15. For example, the controlling circuitry 18 displays a line chart representing the power input to the MTI filter in a dotted line, and representing the power after output from the MTI filter in a solid line in the subarea D3, as illustrated in FIG. 15. The power line chart displayed in the subarea D3 is updated every time the frame is updated.

While the ordinary Doppler mode uses fixed MTI filter characteristics, the MTI filter characteristics are changed among the frames according to the first and the second embodiments. The operator is, however, incapable of understanding which MTI filter with what kind of characteristics has been applied to the frame currently being displayed.

To address this issue, in the third embodiment, control is performed to provide the screen as illustrated in FIG. 15. In this manner, the operator can understand the MTI filter with what kind of characteristics has been applied to the frame currently being displayed. For example, the operator can understand which part is removed as tissues and which part is used as the blood flow information, by referring to the subarea D1. As a result, the operator can understand objectively under which condition the piece of Doppler image data has been acquired for the frame currently being displayed. Furthermore, the operator can also understand the tissue movements resulting from heart beats, or the tissue movements resulting from the movement of the ultrasound probe 1, by referring to the area D and the area E.

The operator who has referred to the information related to the MTI filter matrix may want to change the conditions for generating the Doppler image data. The controlling circuitry 18 therefore may perform the control process explained below. When a request for modifying a parameter used in calculating the filter coefficient is received from an operator who has referred to the information related to the filter coefficient, the controlling circuitry 18 causes the computing circuitry 142 to recalculate the filter coefficient using the modified parameter. Specifically, when request for modifying a parameter used in calculating the MTI filter matrix is received from an operator who has referred to the information related to the MTI filter matrix, the controlling circuitry 18 causes the computing circuitry 142 to recalculate the filter matrix using the modified parameter. Examples of the parameter to be modified include the rank to be reduced, the algorithm for determining the rank to be reduced, and the threshold used in determining the rank to be reduced. The computing circuitry 142 recalculates the MTI filter matrix based on, for example, the modified rank to be reduced. As a result, the Doppler processing circuitry 14 outputs Doppler data that is based on the modified parameter, and the image generating circuitry 15 generates Doppler image data that is based on the modified parameter. With such control, the operator can observe the blood flow information in the image quality desired by the operator.

Fourth Embodiment

Figure 16:
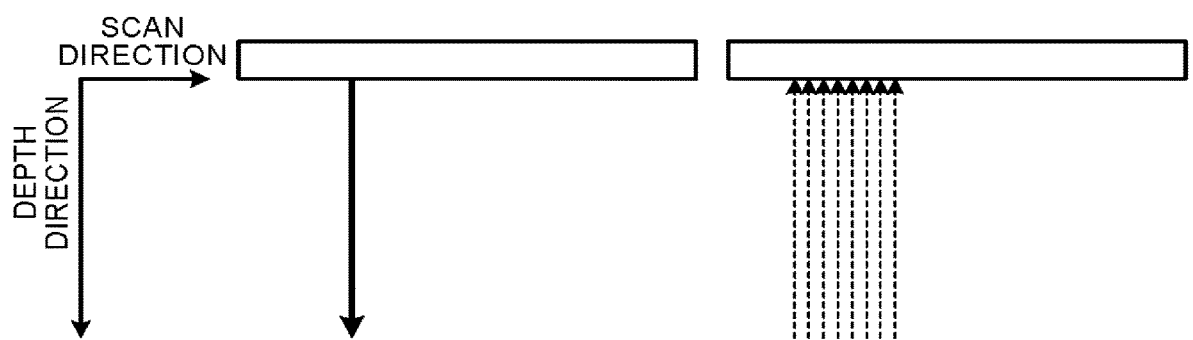
FIG. 16 and FIG. 17 are schematics for explaining the fourth embodiment.
Figure 17:
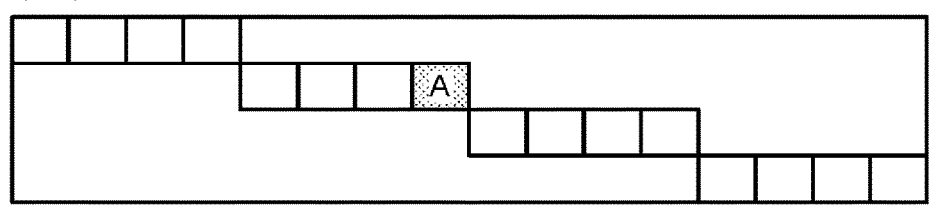
Figure 17:
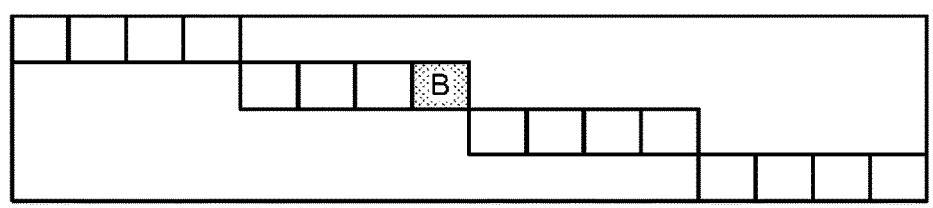
Figure 17:
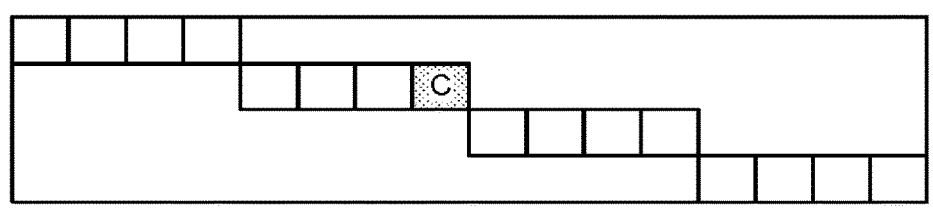

In a fourth embodiment, a modification of the "high-frame-rate ultrasound scan" explained in the first to the third embodiments will be explained with reference to FIGS. 16 and 17. FIGS. 16 and 17 are schematics for explaining the fourth embodiment.

The controlling circuitry 18 according to the fourth embodiment executes the "high-frame-rate ultrasound scan" explained in the first to the third embodiments by receiving reflection wave beams simultaneously and parallelly. For example, the controlling circuitry 18 controls to receive eight beams simultaneously and parallelly, as illustrated in FIG. 16. In FIG. 16, the central axis of the transmitted ultrasonic wave in the depth direction is indicated by the arrow in a solid line, and eight reflection wave beams received simultaneously in a first run is indicated by the arrows in a dotted line. In one ultrasonic wave transmission and reception, the transmitting and receiving circuitry 11 receives reflection wave signals for the eight scan lines from the ultrasound probe 1. In this manner, the transmitting and receiving circuitry 11 can generate a set of received signals (reflection wave data set) for the eight scan lines, based on one ultrasonic wave transmission and reception, and output the received signals to the Doppler processing circuitry 14.

In FIG. 17, the horizontal direction represents the raster direction (scan direction), and the vertical direction represents the temporal direction (frame direction). In the example illustrated in FIG. 17, the number of scan lines making up the first scanned region (the number of rasters) is 16, and reflection waves in four directions is received simultaneously and parallelly. In the example illustrated in FIG. 17, because the number of scan lines is 16, and the number of beams received simultaneously and parallelly are four, the first scanned region is divided into four sections each consisting of four scan lines (a first section, a second section, a third section, and a fourth section).

The ultrasound probe 1 transmits an ultrasonic wave along a transmission scan line at the center of the first section in the raster direction, and receives the reflection wave in the four directions simultaneously, along the respective scan lines making up the first section. In this manner, four received signals are generated for the first section. The same process is performed for the second section, the third section, and the fourth section, and received signals for 16 scan lines making up the first scanned region are acquired. "A", "B", and "C" illustrated in FIG. 17 represent received signals (reflection wave data) from the same position in a frame (n−2), a frame (n−1), and a frame n, respectively. The Doppler processing circuitry 14 can perform the process explained in the first to the third embodiments using the data array "A", "B", and "C" from the same position in these consecutive frames.

As described above, in the fourth embodiment, by receiving reflection wave beams simultaneously and parallelly in the "high-frame-rate ultrasound scan", the frame rate (or volume rate) at which the Doppler image data is displayed can be improved further. The number of reflection wave beams received simultaneously and parallelly can be set to any number in a manner suitable for the required frame rate (or volume rate), within the range below the upper limit at which the transmitting and receiving circuitry 11 is capable of receiving simultaneously and parallelly.

Fifth Embodiment

Figure 18:
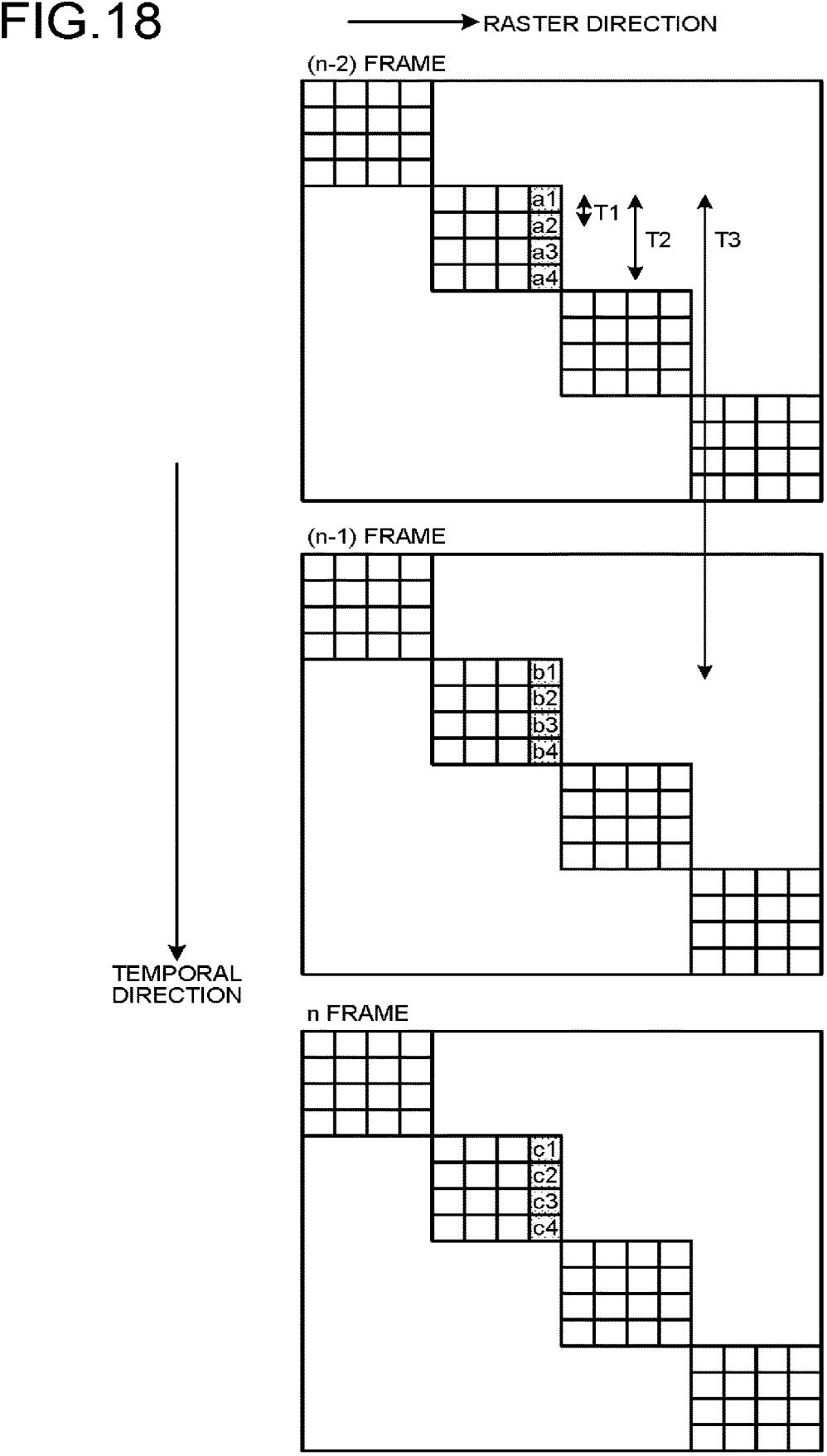
FIG. 18 and FIG. 19 are schematics for explaining the fifth embodiment.
Figure 19:
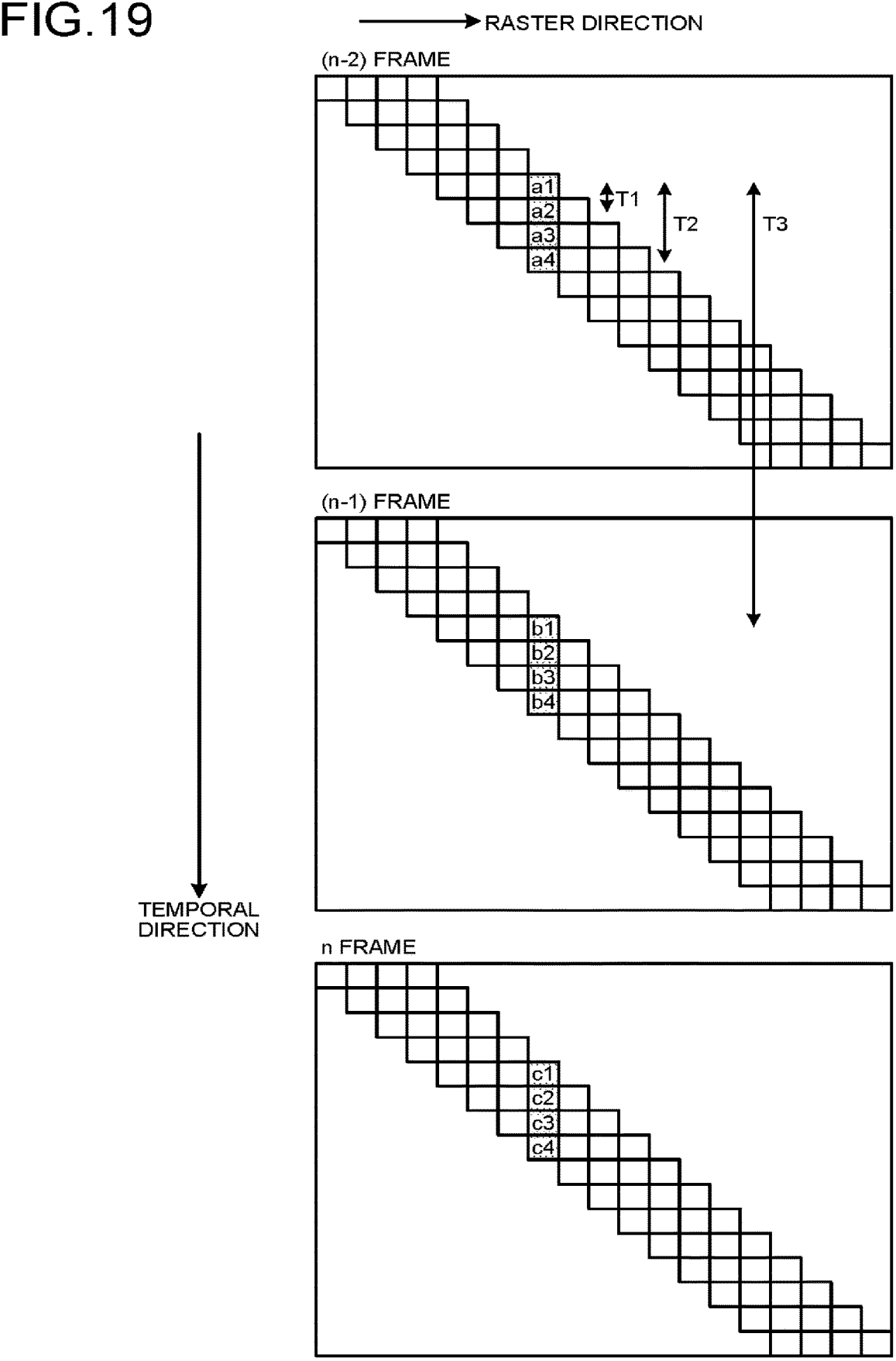

Explained in a fifth embodiment with reference to FIGS. 18 and 19 is a type of scan other than the "high-frame-rate ultrasound scan" that can be used in the image processing method explained in the first to the third embodiments. FIGS. 18 and 19 are schematics for explaining the fifth embodiment.

The scan used in the first ultrasound scan according to the fifth embodiment aims to collect a data array of consecutive pieces of reflection wave data from the same position in the frame direction, in the same manner as the scan explained in the first to the fourth embodiments. The controlling circuitry 18 according to the fifth embodiment, however, performs the ultrasound scan in which an ultrasonic wave is transmitted and received a plurality of number of times along each of the scan lines, as the first ultrasound scan. The transmitting and receiving circuitry 11 or the Doppler processing circuitry 14 then adds and averages a plurality of received signals corresponding to each of the scan lines, under the control of the controlling circuitry 18 according to the fifth embodiment. In this manner, reflection wave data can be acquired for each of a plurality of scan lines making up the first scanned region. The Doppler processing circuitry 14 then performs the process explained in the first to the third embodiments using the data array in the frame direction.

In other words, the consecutive reflection wave data, used by the correlation matrix calculating circuitry 141 according to the fifth embodiment as the data array for calculating the correlation matrix, is collected by repeating the scan in which an ultrasonic wave is transmitted and received a plurality of number of times along each of the scan lines making up the scanned region (first scanned region), and by adding and averaging the pieces of reflection wave data collected for each of the scan lines.

In the first ultrasound scan according to the fifth embodiment, a plurality of received signals are acquired along one scan line. In the first ultrasound scan according to the fifth embodiment, a plurality of received signals acquired along one scan line are added and averaged, and as a result, one received signal (reflection wave data) is output for one scan line. A plurality of received signals added and averaged are signals including phase information, e.g., IQ signals or RF signals. In other words, the adding and averaging process performed in the fifth embodiment is the coherent addition. By performing the coherent addition, the signal-to-noise ratio (S/N) of the received signal can be improved. As a result, in the fifth embodiment, for example, the S/N of the color Doppler image data can be improved.

For example, in the first ultrasound scan according to the fifth embodiment, an ultrasonic wave is transmitted and received four times along each of the scan lines making up the first scanned region. In the first ultrasound scan according to the fifth embodiment, for example, the adding and averaging process is performed on the four pieces of reflection wave data (received signal) acquired along one scan line, and as a result, one received signal (reflection wave data) is output for one scan line. For example, by adding and calculating the average of four received signals, the S/N of the reflection wave data from each of the sampling points on the scan line is improved by "six decibels."

The first ultrasound scan performed in the manner described above results in a lower frame rate, because an ultrasonic wave is transmitted and received four times along each of the scan lines for one frame. To address this issue, in the first ultrasound scan according to the fifth embodiment, the controlling circuitry 18 may perform "a scan in which an ultrasonic wave is transmitted and received a plurality of number of times along each of the scan lines making up the first scanned region, and one piece of reflection wave data for the corresponding scan line is acquired" using the simultaneous parallel receiving.

When the simultaneous parallel receiving is used in the first ultrasound scan according to the fifth embodiment, the controlling circuitry 18 performs the first ultrasound in a first approach or a second approach. In the first approach, the controlling circuitry 18 divides the first scanned region into a plurality of sections in such a manner that adjacent sections do not overlap each other, and allows reflection waves from the respective sections to be received parallelly and simultaneously. In the second approach, the controlling circuitry 18 divides the first scanned region into a plurality of sections in such a manner that adjacent sections overlap each other, and allows reflection waves from the respective sections to be received parallelly and simultaneously.

FIG. 18 illustrates an example of the first ultrasound scan according to the fifth embodiment using the simultaneous parallel receiving based on the first approach. FIG. 19 illustrates an example of the first ultrasound scan according to the fifth embodiment using the simultaneous parallel receiving based on the second approach.

In FIGS. 18 and 19, the horizontal direction represents the raster direction (scan direction), and the vertical direction represents the temporal direction (frame direction), in the same manner as in the example illustrated in FIG. 17 explained in the fourth embodiment. In the example illustrated in FIGS. 18 and 19, in the same manner as in the example explained with reference to FIG. 17, the number of scan lines making up the first scanned region (the number of rasters) is 16, and the reflection waves in four directions are received simultaneously, using the simultaneous parallel receiving. "T1" in FIGS. 18 and 19 represents the sampling cycle. "T2" in FIGS. 18 and 19 represents an addition width. "T3" in FIGS. 18 and 19 represents a frame cycle. The frame cycle "T3" represents the pulse repetition cycle in the ordinary Doppler mode.

In the first approach, as illustrated in FIG. 18, the first scanned region is divided into four sections consisting of four scan lines (a first section, a second section, a third section, and a fourth section), in the same manner as in the example illustrated in FIG. 17. In the first approach, however, simultaneous parallel receiving is repeated four times, for example, in each section, as illustrated in FIG. 18. As a result, as illustrated in FIG. 18, in the frame (n−2), four received signals are acquired from the same position on the same receiving scan line. In FIG. 18, these four pieces of data are denoted by "a1, a2, a3, and a4", respectively. In the same manner, as illustrated in FIG. 18, in the frame (n−1), four received signals are acquired from the same position on the same receiving scan line. In FIG. 18, these four pieces of data are denoted by "b1, b2, b3, and b4", respectively. In the same manner, as illustrated in FIG. 18, in the frame n, four received signals are acquired from the same position on the same receiving scan line. In FIG. 18, these four pieces of data are denoted by "c1, c2, c3, and c4", respectively.

The transmitting and receiving circuitry 11 outputs, for example, "A=(a1+a2+a3+a4)/4". The transmitting and receiving circuitry 11 also outputs "B=(b1+b2+b3+b4)/4", for example. The transmitting and receiving circuitry 11 also outputs "C=(c1+c2+c3+c4)/4". In this manner, the S/N is improved by six decibels, compared with that before the adding and averaging operation. The Doppler processing circuitry 14 then performs the process explained in the first to the third embodiments using the data array "A", "B", and "C" from the same position in these consecutive frames.

In view of the Doppler frequency, by adding four pieces of data, the resultant data is applied with low pass filter (LPF), but the velocity components removed due to the sampling cycle "T1" and the addition width "T2" have sufficiently high frequencies compared with the frame cycle "T3", it would not present any problem in the observations of low flow rates.

In the second approach, for example, as illustrated in FIG. 19, the transmission scan lines are shifted by every scan line at a time, and the reflection waves along four directions are received simultaneously and parallelly. As a result, as illustrated in FIG. 19, four received signals "a1, a2, a3, and a4" from the same position on the same receiving scan line are acquired in the frame (n−2), and "A=(a1+a2+a3+a4)/4" is output, in the same manner as in the first approach. Furthermore, as illustrated in FIG. 19, four received signals "b1, b2, b3, and b4" from the same position on the same receiving scan line are acquired in the frame (n−1), and "B=(b1+b2+b3+b4)/4" is output in the same manner as in the first approach. Furthermore, as illustrated in FIG. 19, four received signals "c1, c2, c3, c4" from the same position on the same receiving scan line are acquired in the frame n, and "C=(c1+c2+c3+c4)/4" is output, in the same manner as in the first approach. In this manner, the S/N is improved by six decibels, compared with that before the adding and averaging operation. Between FIGS. 18 and 19, the frame rate of the Doppler image data remains the same.

In the example illustrated in FIG. 19, when two received signals are acquired for one scan line, the two received signals are added and averaged for the scan line. When three received signals are acquired for one scan line, the three received signals are added and averaged for the scan line. Furthermore, in the example illustrated in FIG. 19, when only one received signal is acquired in one scan line, the one received signal is used as data to be processed by the Doppler processing circuitry 14. Furthermore, in the second approach, the transmission scan lines may be shifted by every two lines, for example, depending on the number of received signals to be added and averaged. The scan used in the second approach can be said to be the same as that explained in the first to the fourth embodiments in that the scan line is switched every time an ultrasonic wave is transmitted and received once.

An advantage of the second approach will now be explained. In the first ultrasound scan in the scan mode using the first approach, the sections, each in which the beams are received simultaneously and parallelly a plurality of number of times, do not overlap one another. In the first approach illustrated in FIG. 18, because the position at which the beam is transmitted along the same scan line to acquire the four received signals remains the same, the phase does not change depending on the transmitting beams. In the first approach illustrated in FIG. 18, however, the sections in each of which beams are received simultaneously and parallelly for four times do not overlap one another. Therefore, in the first approach illustrated in FIG. 18, streak-like artifacts, in units of four rasters, may appear between the sections.

By contrast, in the first ultrasound scan in the scan mode using the second approach, the beams are received simultaneously and parallelly only once in each of the sections overlapping with adjacent sections. In the second approach illustrated in FIG. 19, because the position at which the beams are transmitted to acquire four received signals along the same scan line changes, a very small phase shift may occur. Such phase shift, however, can be removed with the subsequent filtering. Furthermore, in the second approach illustrated in FIG. 19, because each of the sections in which the beams are received simultaneously and parallelly overlap one another by three scan lines, streak-like artifacts does not appear in the resultant image.

As described above, in the fifth embodiment, the correlation matrix and the MTI filter matrix (filter coefficient) are calculated, and the filtering with the MTI filter matrix (filter coefficient) is performed using the received signal (reflection wave data) resulting from the coherent addition of a plurality of received signals acquired along each of the scan lines. As a result, according to the fifth embodiment, while the frame rate is reduced compared with the first ultrasound scan explained in the first to fourth embodiments, the S/N of the reflection wave data for generating images representing blood flow information can be improved. While explained above is an example in which the number of beams received simultaneously and parallelly is four, but this number of beams simultaneously and parallelly received may be any number. Furthermore, as explained at the beginning, the first ultrasound scan according to the fifth embodiment may be implemented without the simultaneous parallel beam receiving. Furthermore, the transmitting and receiving circuitry 11 or the Doppler processing circuitry 14 may apply low-pass filtering similar to the adding and averaging process, to the a plurality of received signals acquired along each of the scan lines, under the control of the controlling circuitry 18 according to the fifth embodiment. Furthermore, the specifics explained in the first to fourth embodiments are also applicable to the fifth embodiment, except for how the first ultrasound scan is performed.

Sixth Embodiment

In the first to the fifth embodiments, eigenvalue of a correlation matrix and eigenvectors corresponding to the respective eigenvalues are calculated, and a matrix resulting from reducing the rank of a matrix consisting of the eigenvectors arranged in the order of eigenvalue size is established as a filter matrix for suppressing the clutter components, as an exemplary way for performing principal component analysis using a correlation matrix, for approximating the clutter components as a principal component, and for reducing the clutter components. In other words, explained in the first to the fifth embodiments is an example in which a matrix (filter matrix) for suppressing clutter components are established by determining the number of diagonal elements set to "zero" in the diagonal matrix, as expressed in Expression (2).

As an alternative way of performing principal component analysis using a correlation matrix, of approximating the clutter components as a principal component, and of reducing the clutter components, a matrix that identifies the clutters may be established. A signal approximating a clutter component as a principal component may then be acquired using the matrix and the original signal, and the resultant signal may be subtracted from the original signal. This alternative may be used in the first to the fifth embodiments.

This alternative will now be explained using some expressions. To explain the approach described specifically in the first embodiment as a method generally referred to as principal component analysis, signals from a dominantly large tissue (clutters) can be extracted as signal components by analyzing the principal components of the correlation matrix and approximating the original signals (input signals) with the principal components. Signals from blood flows can then be extracted by subtracting the signals approximated with the extracted principal components, that is, the clutters from the original signals. This process can be expressed as Expression (14) below.

$$x - V \begin{pmatrix} 1 & & & & \\ & 1 & & & \\ & & \ddots & & \\ & & & 0 & \\ & & & & 0 \end{pmatrix} V^H x \quad (14)$$

"x" in Expression (14) is a column vector representing the original signal. "V" and "$V^H$" in the second term in Expression (14) are the same as those in Expression (2). The number of diagonal elements "one" in the diagonal matrix in the second term in Expression (14) represents the number of principal components approximated. In other words, the second term in Expression (14) is signals representing the clutter components approximated as principal components. Expression (14) indicates that the blood flow signals are extracted from the data array "x" representing the original signals by subtracting the signals approximating the clutter components, represented by the second term, from the original signals.

Expression (14) can be expressed as a product of a filter matrix and the original signal vector, as indicated in following Expression (15).

$$x - V \begin{pmatrix} 1 & & & & \\ & 1 & & & \\ & & \ddots & & \\ & & & 0 & \\ & & & & 0 \end{pmatrix} V^H x = \left\{ I - V \begin{pmatrix} 1 & & & & \\ & 1 & & & \\ & & \ddots & & \\ & & & 0 & \\ & & & & 0 \end{pmatrix} V^H \right\} x = \quad (15)$$

-continued $$\left\{VV^H - V\begin{pmatrix}1 & & & \\ & 1 & & \\ & & \ddots & \\ & & & 0 \\ & & & & 0\end{pmatrix}V^H\right\}x = V\begin{pmatrix}0 & & & \\ & 0 & & \\ & & \ddots & \\ & & & 1 \\ & & & & 1\end{pmatrix}V^H x$$

As indicated by Expression (15), the operation of Expression (14) is equivalent to the operation of Expression (2). In other words, the process of Expression (14) for estimating (extracting) the blood flow information using a filter coefficient identifying the clutters by "ones" in the diagonal matrix is equivalent to the process of estimating (extracting) the blood flow information using a filter coefficient for suppressing the clutters by "zeros" in the diagonal matrix explained in the first to the fifth embodiments. In the manner described above, the image processing method explained in the first to the fifth embodiments may also be implemented by causing the computing circuitry 142 to calculate a matrix (filter coefficient) identifying the clutter components by means of principal component analysis of the correlation matrix. Therefore, the process explained in the sixth embodiment can also improve the image quality of an image visualizing the blood flow information.

In the first to the sixth embodiments described above, the image processing method is explained to be executed by an ultrasonic diagnostic apparatus. However, the image processing method explained in the first to the sixth embodiments may be executed by an image processing apparatus capable of acquiring the reflection wave data (IQ signals) output from the transmitting and receiving circuitry 11.

In the embodiments, elements included in the apparatuses are illustrated in the drawings to schematically depict her functionality, and are not necessarily need to be configured physically in the manner illustrated in the drawings. In other words, specific configurations in which the apparatuses are distributed or integrated are not limited to those illustrated in the drawings, and the whole or a part of the apparatuses may be distributed or integrated functionally or physically in any units depending on various loads or utilization. The whole or a part of the processing functions executed in each of the apparatuses may be achieved as a CPU and a computer program parsed and executed by the CPU, or implemented as hardware using wired logics.

Furthermore, the image processing method explained in the first to the sixth embodiments may be implemented by causing a computer such as a personal computer or a workstation to execute an image processing program prepared in advance. The image processing program can be distributed over a network such as the Internet. Furthermore, the image processing program may be implemented by being recorded in a non-transitory computer-readable recording medium such as a hard disk, a flexible disk (FD), a compact disc read-only memory (CD-ROM), a magneto-optical (MO) disc, a digital versatile his (DVD), or a flash memory such as a universal serial bus (USB) memory or a secure digital (SD) card memory, and causing the computer to read the image processing program from the non-transitory recording medium and to execute the image processing program.

As described above, according to the first to the sixth embodiments, it is possible to improve the image quality of an image of blood flow information visualized with an adaptive MTI filter that uses eigenvectors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
an ultrasound probe configured to transmit and receive an ultrasound wave;
correlation matrix calculating circuitry configured to calculate a correlation matrix of a scanned region consisting of a plurality of scan lines, from a data array of pieces of reflection wave data collected from a same position by transmitting and receiving the ultrasonic wave in the scanned region, in a plurality of frames in a temporal direction;
calculating circuitry configured to calculate a filter matrix for suppressing a clutter component generated by a tissue, by performing principal component analysis using the correlation matrix, and by performing a matrix operation of approximating the clutter component as a principal component and of suppressing the clutter component;
image generating circuitry configured to generate ultrasound image data from blood flow information estimated using the filter matrix; and
controlling circuitry configured to cause a display to display the ultrasound image data, wherein
the calculating circuitry calculates a plurality of eigenvalues of the correlation matrix, and a plurality of eigenvectors corresponding to the plurality of eigenvalues, and calculates the filter matrix from a matrix resulting from reducing a rank of a matrix comprising an arrangement of the plurality of eigenvectors based on a comparison result between a ratio of two values among a plurality of values indicating magnitude of the plurality of eigenvalues and at least one of a plurality of thresholds.

2. The ultrasonic diagnostic apparatus according to claim 1, wherein the correlation matrix calculating circuitry is further configured to use, as the data array, a data array of consecutive pieces of reflection wave data collected from the same position by repeating a scan in which an ultrasonic wave is transmitted and received once along each of the scan lines in the scanned region.

3. The ultrasonic diagnostic apparatus according to claim 2, wherein the controlling circuitry is further configured to execute the scan with simultaneous parallel receiving.

4. The ultrasonic diagnostic apparatus according to claim 1, wherein the correlation matrix calculating circuitry is further configured to use, as the data array, a data array of consecutive pieces of reflection wave data that is collected from the same position by repeating a scan in which the reflection wave data of the respective scan lines making up the scanned region is collected by performing an adding and an averaging process or a low-pass-filtering process similar to the adding and the averaging process to the pieces of reflection wave data collected from each of the scan lines by transmitting and receiving an ultrasonic wave along each of the scan lines a plurality of number of times.

5. The ultrasonic diagnostic apparatus according to claim 4, wherein the controlling circuitry is further configured to execute the scan with simultaneous parallel receiving.

6. The ultrasonic diagnostic apparatus according to claim 5, wherein the controlling circuitry is further configured to execute the simultaneous parallel receiving by dividing the scanned region into a plurality of sections, or execute the simultaneous parallel receiving by dividing the scanned region into the plurality of sections with adjacent sections overlapping one another.

7. The ultrasonic diagnostic apparatus according to claim 1, wherein the calculating circuitry is further configured to change a number of principal components to be reduced based on a size of eigenvalues of the correlation matrix.

8. The ultrasonic diagnostic apparatus according to claim 1, wherein the controlling circuitry is further configured to cause information related to the filter matrix to be output.

9. The ultrasonic diagnostic apparatus according to claim 8, wherein the information related to the filter matrix calculated by the calculating circuitry is at least one of information related to eigenvalues used in calculating the filter matrix, frequency characteristics of the filter matrix, a cutoff frequency of the filter matrix, and power input to and output from the filter matrix.

10. The ultrasonic diagnostic apparatus according to claim 8, wherein the controlling circuitry is further configured to cause the calculating circuitry to re-calculate the filter matrix using a modified parameter, when a request for modifying the parameter used in calculating the filter matrix is received from an operator referring to the information related to the filter matrix.

11. The ultrasonic diagnostic apparatus according to claim 1, wherein a length of the data array from which the correlation matrix is calculated by the correlation matrix calculating circuitry is enabled to be modified, and the data array from which the correlation matrix is calculated is allowed to be used among a plurality of frames to be displayed in an overlapping manner.

12. The ultrasonic diagnostic apparatus according to claim 1, wherein
the correlation matrix calculating circuitry is further configured to calculate a section correlation matrix of each of a plurality of sections that are divisions of the scanned region, and calculate a correlation matrix of each of a plurality of segmented sections that are subdivisions of each of the sections by interpolation using the section correlation matrixes for the respective sections,
the calculating circuitry is further configured to calculate respective filter matrixes for each of the segmented sections from the correlation matrixes for the respective segmented sections, and
the image generating circuitry is further configured to generate the ultrasound image data from the blood flow information estimated using the filter matrixes for the respective segmented sections.

13. An image processing apparatus, comprising:
correlation matrix calculating circuitry configured to calculate a correlation matrix of a scanned region consisting of a plurality of scan lines, from a data array of pieces of reflection wave data collected from a same position by transmitting and receiving an ultrasonic wave in the scanned region, in a plurality of frames in a temporal direction;
calculating circuitry configured to calculate a filter matrix for suppressing a clutter component generated by a tissue, by performing principal component analysis using the correlation matrix, and by performing a matrix operation of approximating the clutter component as a principal component and of suppressing the clutter component;
image generating circuitry configured to generate ultrasound image data from blood flow information estimated using the filter matrix; and
controlling circuitry configured to cause a display to display the ultrasound image data, wherein
the calculating circuitry calculates a plurality of eigenvalues of the correlation matrix, and a plurality of eigenvectors corresponding to the plurality of eigenvalues, and calculates the filter matrix from a matrix resulting from reducing a rank of a matrix comprising an arrangement of the plurality of eigenvectors based on a comparison result between a ratio of two values among a plurality of values indicating magnitude of the plurality of eigenvalues and at least one of a plurality of thresholds.

14. An image processing method, comprising:
calculating, by correlation matrix calculating circuitry, a correlation matrix of a scanned region consisting of a plurality of scan lines, from a data array of pieces of reflection wave data collected from a same position by transmitting and receiving an ultrasonic wave in the scanned region, in a plurality of frames in a temporal direction;
calculating, by calculating circuitry, a filter matrix for suppressing a clutter component generated by a tissue, by performing principal component analysis using the correlation matrix, and by performing a matrix operation of approximating the clutter component as a principal component and of suppressing the clutter component;
generating, by image generating circuitry, ultrasound image data from blood flow information estimated using the filter matrix; and
causing, by controlling circuitry, a display to display the ultrasound image data, wherein
the calculating the filter matrix comprises calculating a plurality of eigenvalues of the correlation matrix, and a plurality of eigenvectors corresponding to the plurality of eigenvalues, and calculating the filter matrix from a matrix resulting from reducing a rank of a matrix comprising an arrangement of the plurality of eigenvectors based on a comparison result between a ratio of two values among a plurality of values indicating magnitude of the plurality of eigenvalues and at least one of a plurality of thresholds.

* * * * *